United States Patent
Saito

(10) Patent No.: US 9,675,287 B2
(45) Date of Patent: Jun. 13, 2017

(54) ENDOSCOPE SYSTEM, ENDOSCOPE SYSTEM PROCESSOR DEVICE, OPERATION METHOD FOR ENDOSCOPE SYSTEM, AND OPERATION METHOD FOR ENDOSCOPE SYSTEM PROCESSOR DEVICE

(71) Applicant: FUJIFILM Corporation, Tokyo (JP)

(72) Inventor: Takaaki Saito, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 271 days.

(21) Appl. No.: 14/613,152

(22) Filed: Feb. 3, 2015

(65) Prior Publication Data
US 2015/0238126 A1    Aug. 27, 2015

(30) Foreign Application Priority Data

Feb. 27, 2014 (JP) .................. 2014-037596
Dec. 19, 2014 (JP) .................. 2014-257364

(51) Int. Cl.
    *A61B 5/1455*     (2006.01)
    *A61B 5/1459*     (2006.01)
    (Continued)

(52) U.S. Cl.
    CPC ........ *A61B 5/1459* (2013.01); *A61B 1/00009* (2013.01); *A61B 1/0638* (2013.01);
    (Continued)

(58) Field of Classification Search
    CPC .............. A61B 5/1455; A61B 5/14551; A61B 5/14552; A61B 5/0075; A61B 1/00009;
    (Continued)

(56) References Cited

U.S. PATENT DOCUMENTS 8,585,586 B2* 11/2013 Yamaguchi ........ A61B 1/00009
                                                             600/109
8,790,251 B2* 7/2014 Yamaguchi ........ A61B 1/00009
                                                             600/118
(Continued)

FOREIGN PATENT DOCUMENTS

JP     2010-69063 A     4/2010
JP     2012-143349 A     8/2012
(Continued)

OTHER PUBLICATIONS

Notice of Reasons for Rejection issued in the corresponding JP Application No. 2014-257364 on Mar. 23, 2016 and an English Translation.

(Continued)

*Primary Examiner* — Eric Winakur
(74) *Attorney, Agent, or Firm* — Birch, Stewart, Kolasch & Birch, LLP

(57) ABSTRACT

The endoscope system includes: an image signal acquisition unit acquiring B1 image signal corresponding to blue narrow band where the amount of light absorption changes according to the oxygen saturation of blood hemoglobin, G2 image signal corresponding to green wavelength band where the amount of light absorption changes according to a blood volume of an observation target, R2 image signal corresponding to red wavelength band where a change in the amount of light absorption with respect to the oxygen saturation or the blood volume is small compared with the B1 and G2 image signal, and B2 image signal corresponding to a wavelength band, a difference between a center wavelength of the wavelength band and a center wavelength of the blue narrow band being 20 to 100 nm; and an oxygen saturation calculation unit calculating the oxygen saturation based on the B1, G2, R3, and B2 image signal.

16 Claims, 18 Drawing Sheets

(51) Int. Cl.
  *A61B 1/00* (2006.01)
  *A61B 1/06* (2006.01)
  *A61B 5/00* (2006.01)
(52) U.S. Cl.
  CPC .......... *A61B 1/0646* (2013.01); *A61B 5/0084* (2013.01); *A61B 5/14551* (2013.01); *A61B 5/7246* (2013.01); *A61B 5/742* (2013.01); *A61B 5/7278* (2013.01); *A61B 5/746* (2013.01)
(58) Field of Classification Search
  CPC ........... A61B 1/04; A61B 1/06; A61B 5/7264; A61B 5/7271; A61B 5/7278
  See application file for complete search history.

(56) References Cited

U.S. PATENT DOCUMENTS

| | | |
|---|---|---|
| 2007/0024946 A1 | 2/2007 | Panasyuk et al. |
| 2012/0116192 A1 | 5/2012 | Saito |
| 2012/0157768 A1* | 6/2012 | Saito ................. A61B 1/00009 600/109 |
| 2012/0176486 A1 | 7/2012 | Maeda et al. |
| 2013/0211217 A1 | 8/2013 | Yamaguchi et al. |

FOREIGN PATENT DOCUMENTS

| | | |
|---|---|---|
| JP | 2012-143398 A | 8/2012 |
| JP | 2012-147928 A | 8/2012 |
| JP | 5191329 B2 | 5/2013 |
| JP | 5231511 B2 | 7/2013 |

OTHER PUBLICATIONS

Extended European Search Report for European Application No. 15152720.7, dated Jul. 16, 2015.

\* cited by examiner

ENDOSCOPE SYSTEM, ENDOSCOPE SYSTEM PROCESSOR DEVICE, OPERATION METHOD FOR ENDOSCOPE SYSTEM, AND OPERATION METHOD FOR ENDOSCOPE SYSTEM PROCESSOR DEVICE

CROSS-REFERENCE TO RELATED APPLICATIONS

The present application claims priority under 35 U.S.C. §119 to Japanese Patent Application No. 2014-037596, filed on Feb. 27, 2014, and Japanese Patent Application No. 2014-257364, filed on Dec. 19, 2014, all of which are hereby expressly incorporated by reference into the present application.

BACKGROUND OF THE INVENTION

1. Field of the Invention

The present invention relates to an endoscope system that images an observation target in a subject, an endoscope system processor device, an operation method for an endoscope system, and an operation method for an endoscope system processor device.

2. Description of the Related Art

In the medical field, it is common to perform diagnosis using an endoscope system including a light source device, an endoscope, and a processor device. In particular, an endoscope system has become widespread that acquires an observation image, in which a specific tissue or structure such as a blood vessel or a ductal structure is emphasized, not only simply by imaging an observation target but also by finding the wavelength of illumination light to be emitted to the observation target or by performing signal processing, such as spectral estimation processing, on an image signal obtained by imaging the observation target. In such an endoscope system, when the observation target is contaminated (due to adhesion of residue or colored mucus, for example) or when dye for coloring is used, a target specific tissue may not be appropriately emphasized, or dirt or the like may be emphasized, for example. Therefore, for example, in an endoscope system for highlighting the blood vessels disclosed in JP5191329B, dye contained in residue or the like is detected based on a spectral estimation image, and an image is generated by correcting the influence of the dye.

In recent years, there has also been an endoscope system that acquires biological function information based on an image signal obtained by imaging the observation target. For example, diagnosis of a lesion using the oxygen saturation of blood hemoglobin has been performed. As a method of acquiring the oxygen saturation, a method is known in which first signal light and second signal light having different wavelength bands and different absorption coefficients for oxygenated hemoglobin and reduced hemoglobin are alternately emitted to blood vessels in the mucous membrane and reflected light beams of the first and second signal light beams are detected by a sensor located at the distal end of the endoscope (refer to JP5231511B).

The ratio of signal values (hereinafter, referred to as a signal ratio) of pixels of an image signal corresponding to the reflected light of the first signal light detected by the sensor and an image signal corresponding to the reflected light of the second signal light detected by the sensor is maintained as a fixed value if there is no change in the oxygen saturation in the blood vessel. However, if there is a change in the oxygen saturation, the signal ratio is also changed accordingly. Therefore, it is possible to calculate the oxygen saturation based on the signal ratio of the image signals.

SUMMARY OF THE INVENTION

Since the oxygen saturation is calculated based on the signal ratio as described above, the calculation accuracy is reduced if the observation target is contaminated with dirt or the like that affects the signal ratio. For example, when the observation target is a mucous membrane of the lower digestive tract, mucus containing yellow (or yellow brown) dye, such as bilirubin or stercobilin, may adhere to the mucous membrane. The yellow dye absorbs light in a blue wavelength band. Accordingly, when the light in the blue wavelength band is used as signal light as disclosed in JP5191329B, signal light is absorbed not only by blood hemoglobin but also by the yellow dye. As a result, the oxygen saturation calculation accuracy may be reduced.

Although the observation target is cleaned in advance, it is not uncommon that there is residue, and mucus containing colored dye may be newly secreted during observation. In addition, the degree of reduction in the oxygen saturation calculation accuracy also differs depending on the amount of adhesion of residue, colored mucus, and the like. Therefore, in order to accurately calculate the oxygen saturation, it is necessary to take into consideration not only the presence of residue, colored mucus, and the like but also the amount.

It is an object of the invention to provide an endoscope system capable of calculating an accurate oxygen saturation even if there is dirt, such as colored mucus, adhering to an observation target, an endoscope system processor device, an operation method for an endoscope system, and an operation method for an endoscope system processor device.

An endoscope system of the invention includes an image signal acquisition unit and an oxygen saturation calculation unit. The image signal acquisition unit acquires a first image signal corresponding to a first wavelength band where an amount of light absorption changes according to oxygen saturation of blood hemoglobin, a second image signal corresponding to a second wavelength band where the amount of light absorption changes according to a blood volume of an observation target, a third image signal corresponding to a third wavelength band where a change in the amount of light absorption with respect to the oxygen saturation is small compared with the first image signal and a change in the amount of light absorption with respect to the blood volume is small compared with the second image signal, and a fourth image signal corresponding to a fourth wavelength band, a difference between a center wavelength of the first wavelength band and a center wavelength of the fourth wavelength band being 20 nm or more and 100 nm or less. The oxygen saturation calculation unit calculates oxygen saturation of the observation target for each pixel based on the first image signal, the second image signal, the third image signal, and the fourth image signal.

It is preferable to further include a signal ratio calculation unit that calculates, for each pixel, a first signal ratio that is a ratio of the first image signal to the second image signal, a second signal ratio that is a ratio of the third image signal to the second image signal, and a third signal ratio that is a ratio of the second image signal to the fourth image signal. In addition, it is preferable that the oxygen saturation calculation unit calculates the oxygen saturation based on the first signal ratio, the second signal ratio, and the third signal ratio.

It is preferable to further include a correlation storage unit that stores a plurality of two-dimensional correlation tables according to a value of the third signal ratio, the two-dimensional correlation tables indicating a correlation between the first and second signal ratios and the oxygen saturation. In this case, it is preferable that the oxygen saturation calculation unit selects the specific correlation table according to the value of the third signal ratio from the plurality of correlation tables and calculates the oxygen saturation using the first and second signal ratios and the selected specific correlation table.

It is preferable to further include a correlation storage unit that stores a three-dimensional correlation table indicating a correlation between the first to third signal ratios and the oxygen saturation. In this case, it is preferable that the oxygen saturation calculation unit calculates the oxygen saturation according to the first to third signal ratios using the three-dimensional correlation table.

It is preferable that the fourth wavelength band includes an isosbestic point at which the amount of light absorption with respect to the oxygen saturation of blood hemoglobin is fixed.

It is preferable to further include a warning notification unit that generates a warning signal for giving a warning when the third signal ratio is a value in a specific range set in advance.

It is preferable to further include: an image generation unit that generates an oxygen saturation image showing the oxygen saturation; and a display image signal generation unit that generates a display image signal for displaying the oxygen saturation image on a display unit. In addition, it is preferable that the display image signal generation unit makes a display in a pixel where the third signal ratio is within the specific range and a display in a pixel where the third signal ratio is outside the specific range different from each other based on the warning signal.

It is preferable that the display image signal generation unit generates the oxygen saturation image in which a color difference signal of the pixel where the third signal ratio is within the specific range is set to zero and a color difference signal of the pixel where the third signal ratio is outside the specific range is set to a value corresponding to the oxygen saturation.

It is preferable that the first and fourth wavelength bands are wavelength bands of 350 nm or more and 500 nm or less. It is preferable that the first and fourth wavelength bands are wavelength bands of 450 nm or more and 650 nm or less.

An endoscope system processor device of the invention includes an image signal acquisition unit and an oxygen saturation calculation unit. The image signal acquisition unit acquires a first image signal corresponding to a first wavelength band where an amount of light absorption changes according to oxygen saturation of blood hemoglobin, a second image signal corresponding to a second wavelength band where the amount of light absorption changes according to a blood volume of an observation target, a third image signal corresponding to a third wavelength band where a change in the amount of light absorption with respect to the oxygen saturation is small compared with the first image signal and a change in the amount of light absorption with respect to the blood volume is small compared with the second image signal, and a fourth image signal corresponding to a fourth wavelength band, a difference between a center wavelength of the first wavelength band and a center wavelength of the fourth wavelength band being 20 nm or more and 100 nm or less. The oxygen saturation calculation unit calculates oxygen saturation of the observation target for each pixel based on the first image signal, the second image signal, the third image signal, and the fourth image signal.

An operation method for an endoscope system of the invention includes an image signal acquisition step and an oxygen saturation calculation step. In the image signal acquisition step, an image signal acquisition unit acquires a first image signal corresponding to a first wavelength band where an amount of light absorption changes according to oxygen saturation of blood hemoglobin, a second image signal corresponding to a second wavelength band where the amount of light absorption changes according to a blood volume of an observation target, a third image signal corresponding to a third wavelength band where a change in the amount of light absorption with respect to the oxygen saturation is small compared with the first image signal and a change in the amount of light absorption with respect to the blood volume is small compared with the second image signal, and a fourth image signal corresponding to a fourth wavelength band, a difference between a center wavelength of the first wavelength band and a center wavelength of the fourth wavelength band being 20 nm or more and 100 nm or less. In the oxygen saturation calculation step, an oxygen saturation calculation unit calculates oxygen saturation of the observation target for each pixel based on the first image signal, the second image signal, the third image signal, and the fourth image signal.

An operation method for an endoscope system processor device of the invention includes an image signal acquisition step and an oxygen saturation calculation step. In the image signal acquisition step, the image signal acquisition unit acquires a first image signal corresponding to a first wavelength band where an amount of light absorption changes according to oxygen saturation of blood hemoglobin, a second image signal corresponding to a second wavelength band where the amount of light absorption changes according to a blood volume of an observation target, a third image signal corresponding to a third wavelength band where a change in the amount of light absorption with respect to the oxygen saturation is small compared with the first image signal and a change in the amount of light absorption with respect to the blood volume is small compared with the second image signal, and a fourth image signal corresponding to a fourth wavelength band, a difference between a center wavelength of the first wavelength band and a center wavelength of the fourth wavelength band being 20 nm or more and 100 nm or less. In the oxygen saturation calculation step, an oxygen saturation calculation unit calculates oxygen saturation of the observation target for each pixel based on the first image signal, the second image signal, the third image signal, and the fourth image signal.

According to the endoscope system, the endoscope system processor device, the operation method for an endoscope system, and the operation method for an endoscope system processor device, it is possible to calculate an accurate oxygen saturation even if there is dirt, such as colored mucus, adhering to the observation target.

DESCRIPTION OF THE PREFERRED EMBODIMENTS

First Embodiment

Figure 1:
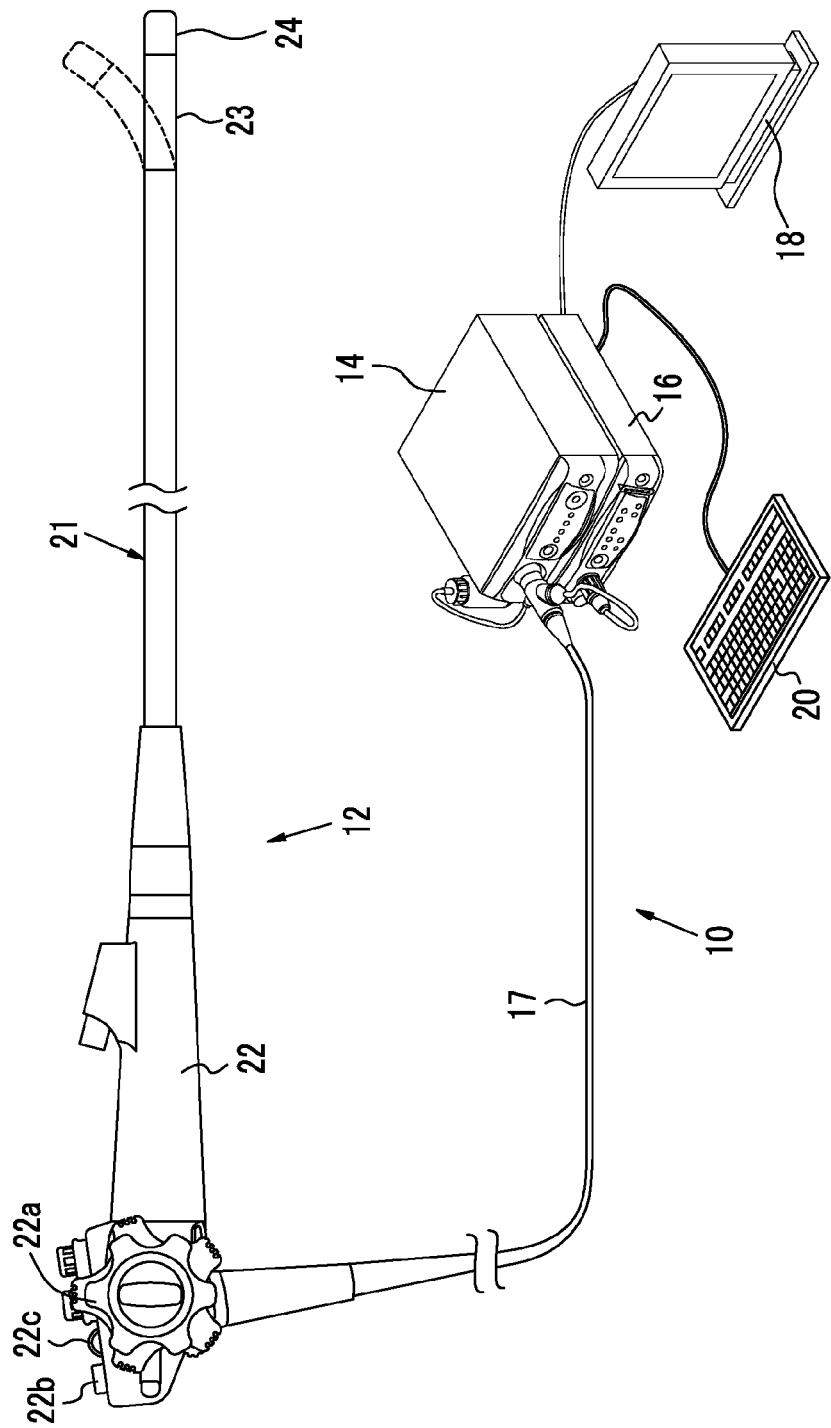
FIG. 1 is an external view of an endoscope system.

As shown in FIG. 1, an endoscope system 10 according to a first embodiment includes an endoscope 12, a light source device 14, a processor device 16, a monitor 18 (display unit), and a console 20. The endoscope 12 is optically connected to the light source device 14, and is electrically connected to the processor device 16. The endoscope 12 includes an insertion unit 21 that is inserted into a subject, an operating unit 22 provided at the base end of the insertion unit 21, and a bending portion 23 and a distal portion 24 that are provided at the distal side of the insertion unit 21. By operating an angle knob 22a of the operating unit 22, the bending portion 23 is bent. The distal portion 24 can be directed in a desired direction by the bending operation.

In addition to the angle knob 22a, an observation mode selector SW (observation mode selector switch) 22b, a zoom operation portion 22c, and a freeze button (not shown) for saving a still image are provided in the operating unit 22. The mode selector SW 22b is used for a switching operation between two modes of the normal observation mode and the special observation mode. The normal observation mode is a mode in which a normal light image obtained by full-color imaging of the observation target in the subject is displayed on the monitor 18. The special observation mode is a mode in which an oxygen saturation image obtained by imaging the oxygen saturation of blood hemoglobin of the observation target is displayed on the monitor 18. The zoom operation portion 22c is used for a zooming operation for driving a zoom lens 47 (refer to FIG. 2) in the endoscope 12 to magnify the observation target.

The processor device 16 is electrically connected to the monitor 18 and the console 20. The monitor 18 displays an image, such as a normal light image or an oxygen saturation image, and information regarding the image (hereinafter, referred to as image information or the like). The console 20 functions as a user interface (UI) for receiving an input operation, such as a function setting. A recording unit (not shown) in which image information or the like is recorded may be connected to the processor device 16.

Figure 2:
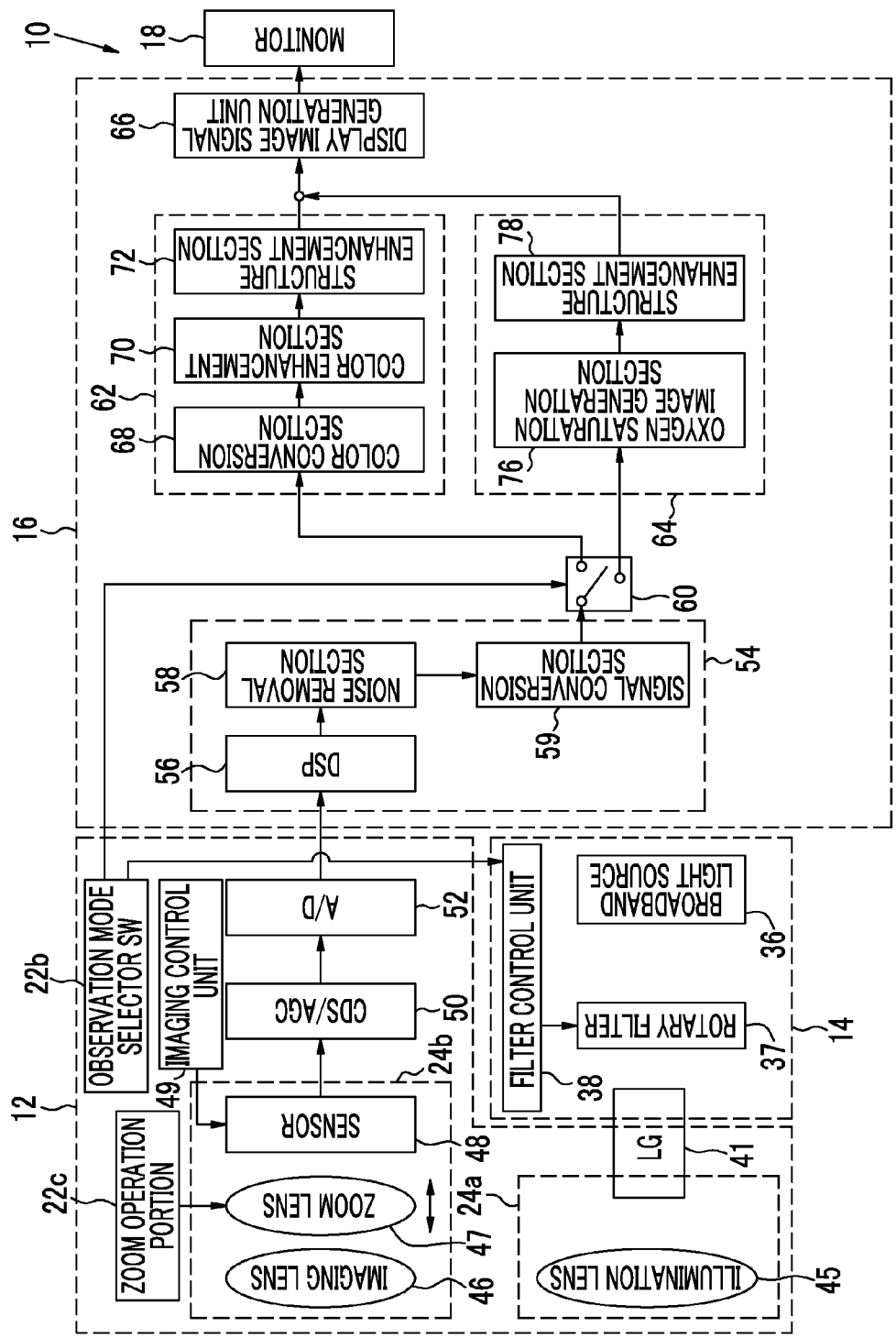
FIG. 2 is a block diagram of the endoscope system.
Figure 3:
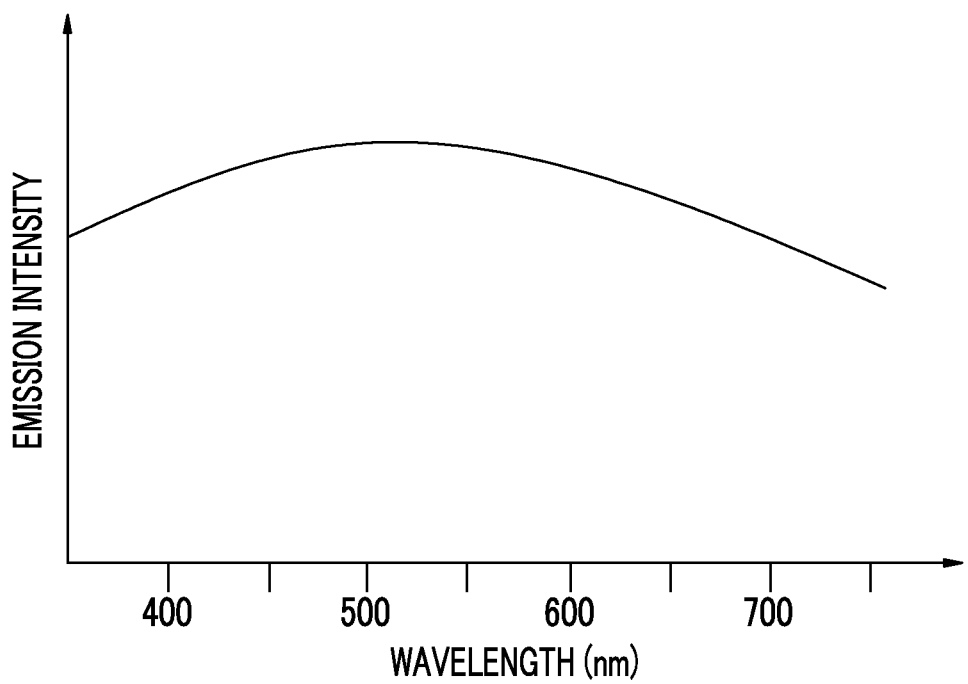
FIG. 3 is a graph showing the spectrum of white light.

As shown in FIG. 2, the light source device 14 includes a broadband light source 36, a rotary filter 37, and a filter control unit 38. The broadband light source 36 is, for example, a xenon lamp or a white light emitting diode (LED), and emits white light in a wavelength band ranging from blue to red as shown in FIG. 3. The white light emitted from the broadband light source 36 is incident on a light guide (LG) 41 through optical members, such as a condensing lens, an optical fiber, and a multiplexer (none are shown) or the rotary filter 37. The light guide 41 is built into a universal cord 17 that connects the endoscope 12 and the light source device 14 to each other (refer to FIG. 1) and the endoscope 12. The light guide 41 causes the incident light to propagate to the distal portion 24 of the endoscope 12. As the light guide 41, a multi-mode fiber can be used. As an example, it is possible to use a small-diameter fiber cable having a diameter of ϕ0.3 mm to ϕ0.5 mm that includes a core with a diameter of 105 μm, a cladding with a diameter of 125 μm, and a protective layer as an outer skin.

Figure 4:
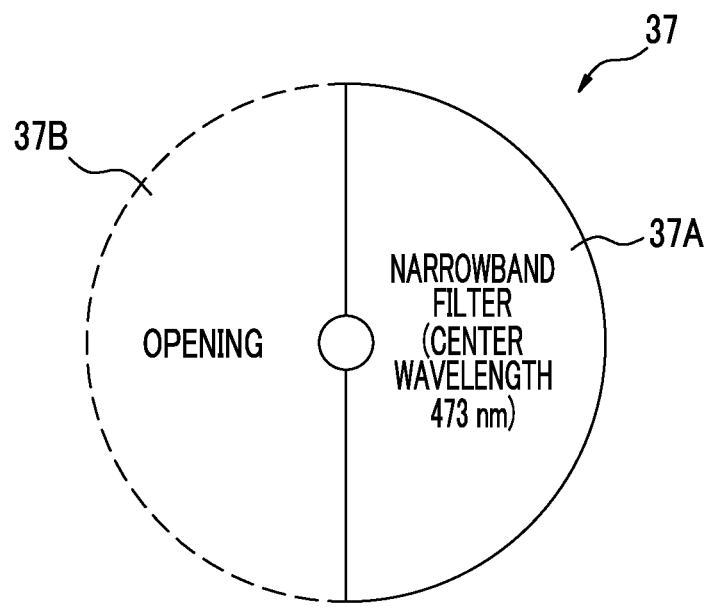
FIG. 4 is an explanatory diagram of a rotary filter.

The rotary filter 37 is rotatably disposed on the optical path along which the white light generated by the broadband light source 36 is incident on the light guide 41. As shown in FIG. 4, the rotary filter 37 includes a narrowband filter 37A and an opening 37B. The narrowband filter 37A limits the wavelength band of light to be transmitted therethrough to light having a center wavelength of 473±10 nm (hereinafter, referred to as blue narrowband light) that is a wavelength band where the amount of light absorption changes according to the oxygen saturation of blood hemoglobin, and cuts light in other wavelength bands. Therefore, when the narrowband filter 37A is disposed on the optical path, only the blue narrowband light of the white light emitted from the broadband light source 36 is transmitted through the narrowband filter 37A and is then incident on the light guide 41. In this case, illumination light emitted to the observation target is the blue narrowband light. On the other hand, when the opening 37B is disposed on the optical path, the white light emitted from the broadband light source 36 is incident on the light guide 41 as it is. In this case, illumination light emitted to the observation target is the white light.

The filter control unit 38 controls the rotation of the rotary filter 37. In the special observation mode, the filter control unit 38 rotates the rotary filter 37 in synchronization with the imaging timing of the observation target. Accordingly, the narrowband filter 37A and the opening 37B alternately pass through the optical path of the white light emitted from the broadband light source 36, and the blue narrowband light and the white light are alternately emitted to the observation target. On the other hand, in the normal observation mode, the filter control unit 38 stops the rotation of the rotary filter 37 in a state where the opening 37B is disposed on the optical path of the white light emitted from the broadband light source 36. As a result, in the normal observation mode, the white light is emitted to the observation target.

The broadband light source 36 and the rotary filter 37 form a light source that generates illumination light to irradiate the observation target. In the present embodiment, the filter control unit 38 controls the rotation and stop of the rotary filter 37 as described above. However, when the rotary filter 37 is provided so as to be retractable from the optical path of the white light, the filter control unit 38 may retract the rotary filter 37 in the normal observation mode, so that the white light is directly incident on the light guide 41 without passing through the rotary filter 37.

The distal portion 24 of the endoscope 12 includes an illumination optical system 24a and an imaging optical system 24b. An illumination lens 45 is provided in the illumination optical system 24a, and the white light or the blue narrowband light from the light guide 41 is emitted to the observation target through the illumination lens 45.

The imaging optical system 24b of the endoscope 12 includes an imaging lens 46, the zoom lens 47, and a sensor 48 (refer to FIG. 2). Reflected light from the observation target is incident on the sensor 48 through the imaging lens 46 and the zoom lens 47. Then, a reflected image of the observation target is formed on the sensor 48. The zoom lens 47 is moved between the tele end and the wide end by operating the zoom operation portion 22c. When the zoom lens 47 is moved to the tele end side, the reflected image of the observation target is magnified. On the other hand, when the zoom lens 47 is moved to the wide end side, the reflected image of the observation target is reduced. When magnified observation is not performed (at the time of non-magnified observation), the zoom lens 47 is disposed at the wide end. When performing magnified observation, the zoom lens 47 is moved from the wide end to the tele end side by operating the zoom operation portion 22c.

The sensor 48 is a color imaging device, and captures a reflected image of the observation target and outputs the image signal. As the sensor 48, for example, a charge coupled device (CCD) image sensor or a complementary metal oxide semiconductor (CMOS) image sensor can be used. In the present embodiment, the sensor 48 is a CCD image sensor. In addition, the sensor 48 includes RGB pixels in which RGB color filters are provided on the imaging surface, and outputs image signals of three colors of R, and B by performing photoelectric conversion in the pixels of respective colors of RGB.

Figure 5:
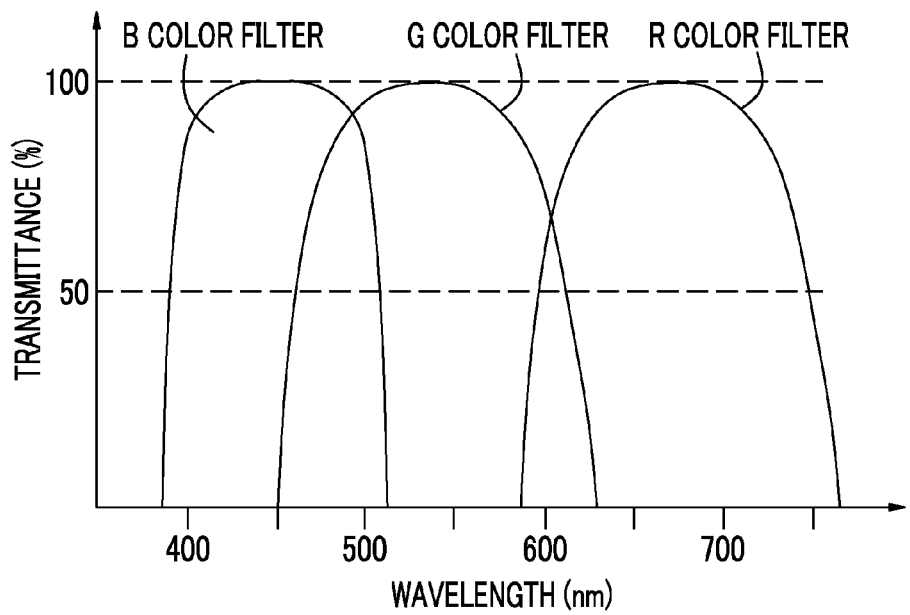
FIG. 5 is a graph showing the spectral transmittance of an RGB color filter.

As shown in FIG. 5, the B color filter has a spectral transmittance of 390 nm to 510 nm, and the center wavelength of the wavelength band of light transmitted through the B color filter is set to 450 nm in the present embodiment. The center wavelength of the B color filter is preferably set such that the difference between the center wavelength of the B color filter and the center wavelength of the wavelength band (473±10 nm) of the blue narrowband light is 20 nm or more and 100 nm or less. The G color filter has a spectral transmittance of 450 nm to 630 nm, and the R color filter has a spectral transmittance of 580 nm to 760 nm. Accordingly, the G color filter transmits light in a wavelength band where the amount of light absorption changes according to the blood volume of the observation target, and the R color filter transmits light in a wavelength band where a change in the amount of light absorption according to the oxygen saturation and the blood volume is smaller than that for the B color filter or the G color filter.

The sensor 48 includes color filters having the characteristics described above. Therefore, when the blue narrowband light is emitted to the observation target as illumination light, an image signal corresponding to the reflected light of the blue narrowband light is obtained from at least the B pixel. On the other hand, when the white light is emitted to the observation target, an image signal corresponding to the color filter of each color is obtained from each of RGB pixels.

As the sensor 48, it is also possible to use a so-called complementary color image sensor including complementary color filters of C (cyan), M (magenta), Y (yellow), and G (green) on the imaging surface. When using the complementary color image sensor as the sensor 48, a color converter that performs color conversion from image signals of four colors of CMYG to image signals of three colors of RGB is preferably provided in the endoscope 12, the light source device 14, or the processor device 16. In this manner, even when complementary color image sensors are used, it is possible to obtain the image signals of three colors of RGB from the image signals of four colors of CMYG by color conversion.

Figure 6:
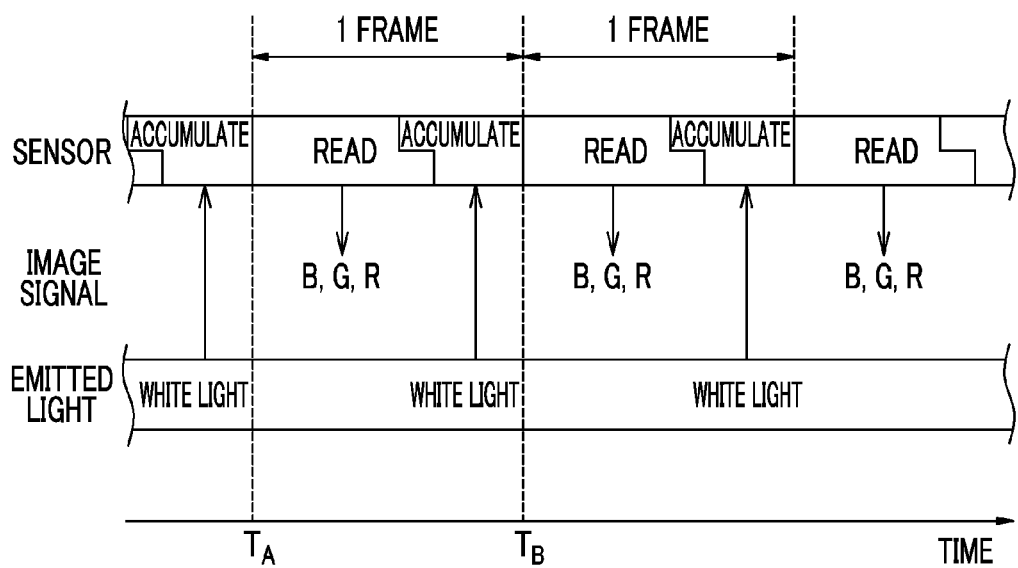
FIG. 6 is an explanatory diagram showing imaging control in the normal observation mode.

An imaging control unit 49 performs imaging control of the sensor 48. As shown in FIG. 6, in the normal observation mode, an observation target illuminated by white light is imaged by the sensor 48 for each period of one frame (hereinafter, simply referred to as one frame). Then, the image signals of RGB are output from the sensor 48 for each frame. In the present embodiment, the sensor 48 is a CCD image sensor. Accordingly, one frame is a period of the length from the end (time $T_A$) of a charge accumulation period (also referred to as an exposure period) to the end of the next charge accumulation period (time $T_B$), for example. In addition, since the sensor 48 is a CCD image sensor, one frame is divided into a reading period and a charge accumulation period in FIG. 6. However, the approximately entire one frame can be set as a charge accumulation period, and signal charges accumulated in the previous frame can also be read during the accumulation of signal charges. The imaging control unit 49 also performs control, such as the adjustment of the length of the charge accumulation period.

Figure 7:
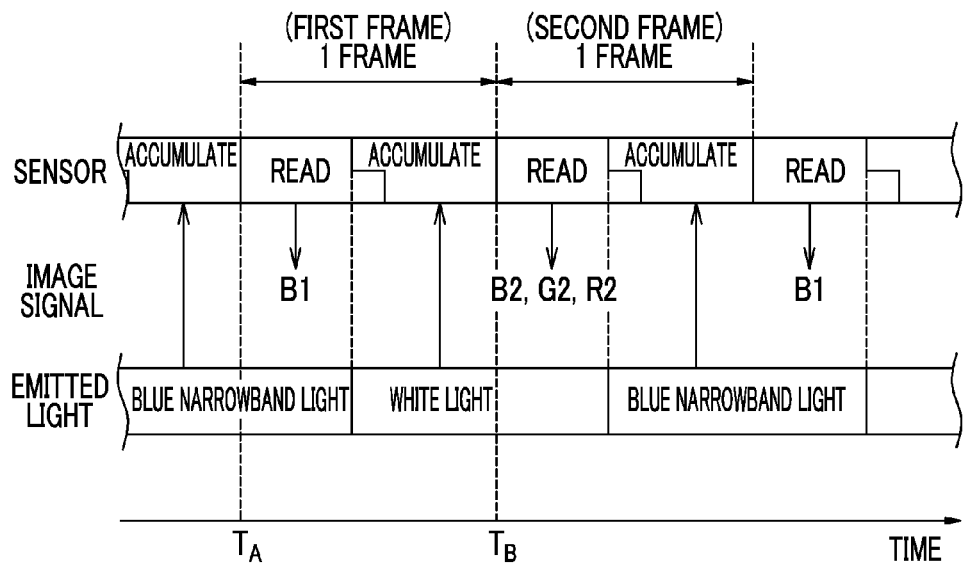
FIG. 7 is an explanatory diagram showing imaging control in the special observation mode.

Also in the special observation mode, the imaging control unit 49 performs imaging control of the sensor 48 in the same manner as in the normal observation mode. However, in the special observation mode, the blue narrowband light and the white light are alternately emitted to the observation target in synchronization with the imaging frame of the sensor 48. Therefore, as shown in FIG. 7, the sensor 48 reads signal charges, which are obtained by imaging the observation target under the blue narrowband light, in the reading period of the first frame, and outputs the image signal from at least the B pixel. Then, the sensor 48 reads signal charges, which are obtained by imaging the observation target under the white light, in the reading period of the second frame, and outputs the image signals of RGB colors. The sensor 48 outputs the image signals of RGB colors in both the first and second frames. However, the spectrum of illumination light in the first frame and the spectrum of illumination light in the second frame are different. Therefore, for the sake of distinction, an image signal that the sensor 48 outputs from the B pixel in the first frame is referred to as a B1 image signal. Although not used in the present embodiment, image signals output from the R and G pixels in the first frame are referred to as an R1 image signal and a G1 image signal, respectively. Image signals of RGB colors output in the second frame are referred to as an R2 image signal, a G2 image signal, and a B2 image signal, respectively.

The B1 image signal is a first image signal corresponding to the wavelength band (first wavelength band) of the blue narrowband light where the amount of light absorption changes according to the oxygen saturation of blood hemoglobin. In addition, the G2 image signal is a second image signal corresponding to the wavelength band (second wavelength band) of the G color filter where the amount of light absorption changes according to the blood volume of the observation target, and the R2 image signal is a third image signal corresponding to the wavelength band (third wavelength band) of the R color filter where a change in the amount of light absorption according to the oxygen saturation and the blood volume is small. In the present embodiment, the G2 image signal is used as an image signal to be a reference of the B1 image signal or the R2 image signal, and is accordingly used for standardization of the B1 image signal or the R2 image signal. However, other image signals may also be used for standardization. The B2 image signal is a fourth image signal corresponding to the wavelength band (fourth wavelength band) of the B color filter.

In order to calculate the oxygen saturation, a signal ratio B1/G2 (first signal ratio) between the B1 image signal and the G2 image signal, a signal ratio R2/G2 (second signal ratio) between the R2 image signal and the G2 image signal, and a signal ratio G2/B2 (third signal ratio) between the G2 image signal and the B2 image signal are used. Among these signal ratios, the signal ratio B1/G2 between the B1 image signal and the G2 image signal using the B1 image signal corresponding to the wavelength band of the blue narrowband light is a signal ratio that is required for the calculation of the oxygen saturation. For this reason, the blue narrowband light is first signal light for calculating the oxygen saturation, and a component (component transmitted through the G color filter) that becomes the G2 image signal in the white light is second signal light for calculating the oxygen saturation.

The image signals of the respective colors output from the sensor 48 are transmitted to a correlated double sampling (CDS)/automatic gain control (AGC) circuit 50 (refer to FIG. 2). The CDS/AGC circuit 50 performs correlated double sampling (CDS) or automatic gain control (AGC) for the analog image signals output from the sensor 48. The image signals transmitted through the CDS/AGC circuit 50 are converted into digital image signals by an A/D converter 52. The image signals that have been digitized in this manner are input to the processor device 16.

The processor device 16 includes an image signal acquisition unit 54, an image processing switching unit 60, a normal observation image processing unit 62, a special observation image processing unit 64, and a display image signal generation unit 66. The image signal acquisition unit 54 receives an image signal input from the endoscope 12. The image signal acquisition unit 54 includes a digital signal processor (DSP) 56, a noise removal section 58, and a signal conversion section 59.

The DSP 56 performs various kinds of signal processing, such as defect correction processing, offset processing, gain correction processing, linear matrix processing, gamma conversion processing, demosaic processing, and YC conversion processing, on the received image signal. A signal of the defective pixel of the sensor 48 is corrected by the defect correction processing. In the offset processing, a dark current component is removed from the image signal subjected to the defect correction processing, and the exact zero level is set. In the gain correction processing, the signal level of each image signal is adjusted by multiplying each of the RGB image signals after the offset processing by a specific gain. Linear matrix processing for increasing color reproducibility is performed on the image signal of each color after the gain correction processing. Then, the brightness or saturation of each image signal is adjusted by gamma conversion processing. Demosaic processing (also referred to as isotropic processing or synchronization processing) is performed on the image signal after the linear matrix processing, and the missing color signal of each pixel is generated by interpolation. Through the demosaic processing, all pixels have signals of RGB colors. The DSP 56 performs YC conversion processing on each image signal after the demosaic processing, and outputs a brightness signal Y and color difference signals Cb and Cr to the noise removal section 58.

The noise removal section 58 performs noise removal processing using, for example, a moving average method or a median filter method on the image signal subjected to the demosaic processing or the like by the DSP 56. The image signals after noise has been removed are input to the signal conversion section 59, are reconverted into RGB image signals, and are input to the image processing switching unit 60.

When the observation mode selector SW 22b is set to the normal observation mode, the image processing switching unit 60 inputs the image signals to the normal observation image processing unit 62. On the other hand, when the observation mode selector SW 22b is set to the special observation mode, the image processing switching unit 60 inputs the image signals to the special observation image processing unit 64.

The normal observation image processing unit 62 includes a color conversion section 68, a color enhancement section 70, and a structure enhancement section 72. The color conversion section 68 generates RGB image data by assigning the input RGB image signals of one frame to R, G, and B pixels. Then, color conversion processing, such as 3×3 matrix processing, gradation conversion processing, and three-dimensional LUT processing, is performed on the RGB image data.

The color enhancement section 70 performs various kinds of color enhancement processing on the RGB image data after the color conversion processing. The structure enhancement section 72 performs structure enhancement processing, such as spatial frequency enhancement, on the RGB image data after the color enhancement processing. The RGB image data subjected to the structure enhancement processing by the structure enhancement section 72 is input to the display image signal generation unit 66 as a normal observation image.

The special observation image processing unit 64 includes an oxygen saturation image generation section 76 and a structure enhancement section 78. The oxygen saturation image generation section 76 calculates the oxygen saturation, and generates an oxygen saturation image indicating the calculated oxygen saturation.

The structure enhancement section 78 performs structure enhancement processing, such as spatial frequency enhancement processing, on the oxygen saturation image input from the oxygen saturation image generation section 76. The oxygen saturation image subjected to the structure enhancement processing by the structure enhancement section 72 is input to the display image signal generation unit 66.

The display image signal generation unit 66 converts the normal observation image or the oxygen saturation image into a display format signal (display image signal), and inputs the display format signal to the monitor 18. As a result, the normal observation image or the oxygen saturation image is displayed on the monitor 18.

Figure 8:
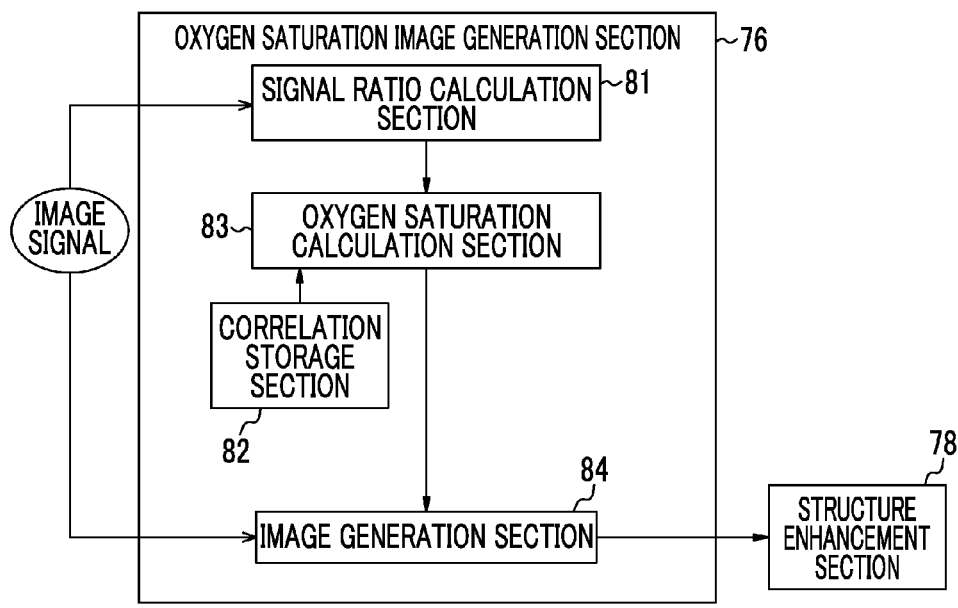
FIG. 8 is a block diagram of an oxygen saturation image generation section and a diagnostic information calculation unit.

As shown in FIG. 8, the oxygen saturation image generation section 76 includes a signal ratio calculation section 81, a correlation storage section 82, an oxygen saturation calculation section 83, and an image generation section 84.

The signal ratio calculation section 81 calculates a signal ratio that is used when the oxygen saturation calculation section 83 calculates the oxygen saturation. Specifically, the signal ratio calculation section 81 calculates the signal ratio B1/G2 between the B1 image signal and the G2 image signal, the signal ratio R2/G2 between the R2 image signal and the G2 image signal, and the signal ratio G2/B2 between the G2 image signal and the B2 image signal for each pixel.

The correlation storage section 82 stores a table of correlation between each signal ratio calculated by the signal ratio calculation section 81 and the oxygen saturation. This correlation table is stored in a three-dimensional manner in which the isosurfaces of the oxygen saturation are defined on the three-dimensional space shown in FIG. 9. The position and shape of each isosurface with respect to the signal ratio are obtained in advance by physical simulation of light scattering. For example, as can be seen from the cross-section of isosurfaces when the signal ratio G2/B2 shown in FIG. 10 is an arbitrary value, a distance between isosurfaces changes according to the signal ratio R2/G2 indicating the blood volume. As can be seen from FIGS. 9 and 10, the position of each isosurface with respect to the signal ratio B1/G2 and the signal ratio R2/G2 changes according to the signal ratio G2/B2 corresponding to the amount (or concentration) of yellow dye, such as bilirubin. That is, if the signal ratios G2/B2 are different even if the signal ratio B1/G2 and the signal ratio R2/G2 are the same value, the values of corresponding oxygen saturation are different. In addition, the correlation between the signal ratio and the oxygen saturation is stored in a log scale.

Figure 11:
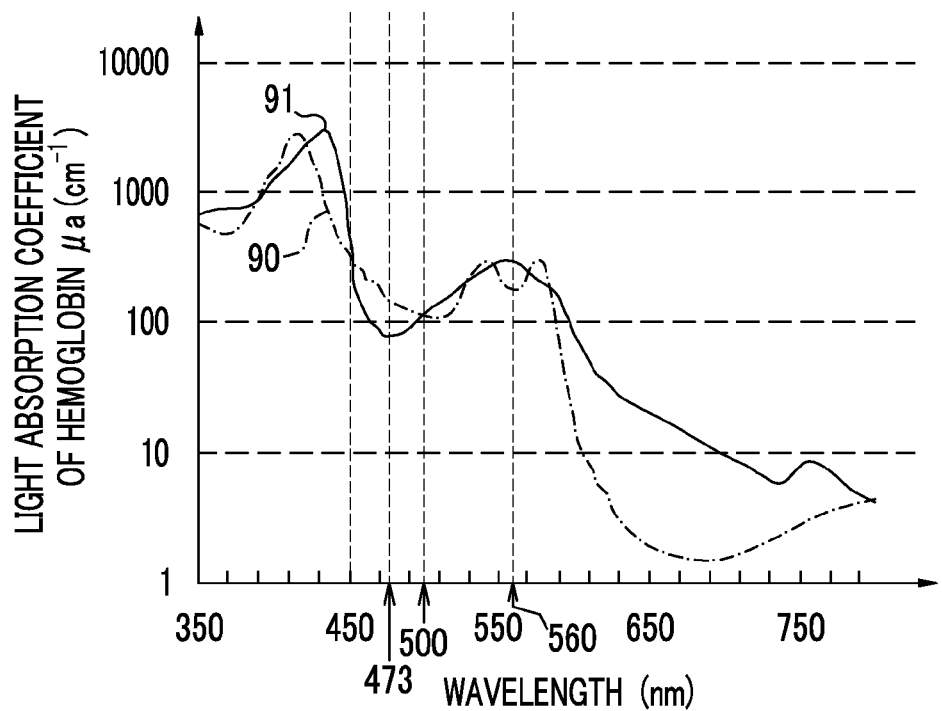
FIG. 11 is a graph showing the absorption coefficients of oxygenated hemoglobin and reduced hemoglobin.

The above correlation is closely related to the absorption characteristics or light scattering characteristics of oxygenated hemoglobin (graph 90) or reduced hemoglobin (graph 91) shown in FIG. 11. For example, as at a center wavelength of 473 nm of the blue narrowband light, at a wavelength at which the difference between the absorption coefficient of oxygenated hemoglobin and the absorption coefficient of reduced hemoglobin is large, it is easy to handle the information of the oxygen saturation. However, the B1 image signal corresponding to 473-nm light has a high dependence not only on the oxygen saturation but also on the blood volume. Therefore, by using the signal ratio R2/G2 obtained from the R2 image signal and the G2 image signal as well as the B1 image signal, it is possible to accurately calculate the oxygen saturation without there being dependency on the blood volume. Here, the G2 image signal corresponds to light that changes mainly depending on the blood volume, and the R2 image signal is a reference signal of the B1 image signal and the G2 image signal.

Figure 12:
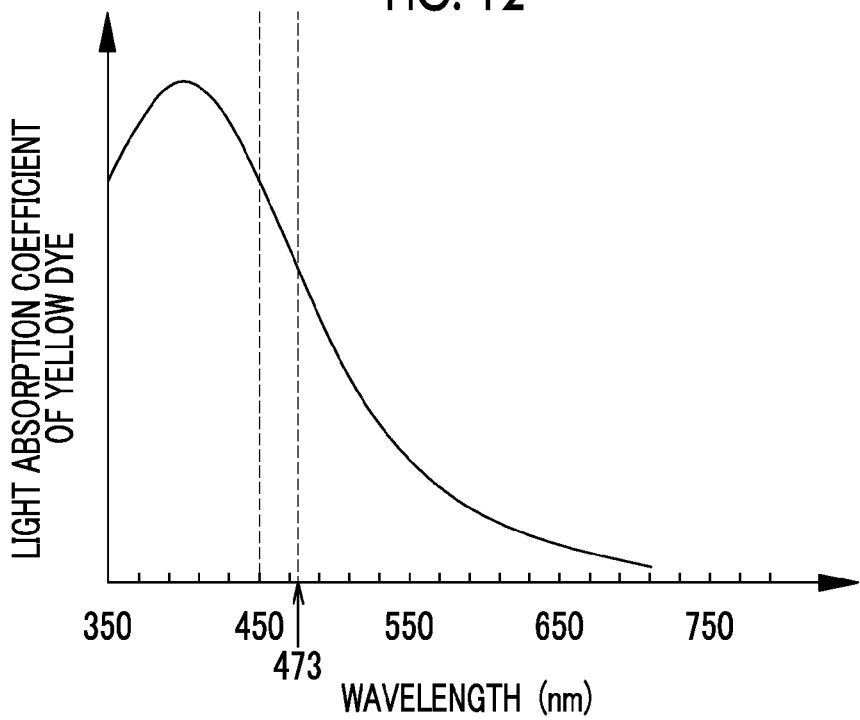
FIG. 12 is a graph showing the typical absorption coefficient spectrum of yellow dye.

In addition, the above correlation is closely related to the light absorption characteristics or light scattering characteristics of yellow dye, such as bilirubin or stercobilin contained in residue or mucus. For example, the absorption coefficient of such yellow dye has a spectrum that gradually decreases with respect to the wavelength, in general, as shown in FIG. 12. At the center wavelength of 473 nm of the blue narrowband light at which the difference between the absorption coefficient of oxygenated hemoglobin and the absorption coefficient of reduced hemoglobin is large, the amount of light absorption of the yellow dye is also large. The influence of yellow dye changes according to the relationship between the yellow dye and the blood volume.

Therefore, by using not only the signal ratio B1/G2 and the signal ratio R2/G2 but also the signal ratio G2/B2 between the B2 image signal and the G2 image signal, it is possible to calculate an accurate oxygen saturation regardless of the presence or absence of yellow dye or the concentration of yellow dye. Here, the B2 image signal corresponds to light in a wavelength band satisfying three conditions that the absorption coefficient of blood hemoglobin is close to that for the blue narrowband light, the scattering coefficient due to the observation target is close to that for the blue narrowband light, and the absorption coefficient of the yellow dye is significantly different from that for the blue narrowband light, and the G2 image signal corresponds to light that changes depending on the blood volume.

In order to satisfy the condition that the absorption coefficient of blood hemoglobin is close to that for the blue narrowband light and the condition that the scattering coefficient due to the observation target is close to that for the blue narrowband light, it is necessary to use an image signal corresponding to light in a wavelength band as close as possible to the blue narrowband light. In addition to these conditions, in order to satisfy the condition that the absorption coefficient of the yellow dye is significantly different from that for the blue narrowband light, it is necessary to use an image signal corresponding to light in a wavelength band apart from the blue narrowband light to some extent. In consideration of these, by setting the spectral transmittance of the B color filter such that the difference between the center wavelength of light transmitted through the B color filter and the center wavelength of the blue narrowband light is 20 nm or more and 100 nm or less, the B2 image signal satisfying the three conditions described above is obtained. In particular, in order to calculate an accurate oxygen saturation with low dependence on yellow dye by increasing the difference between the absorption coefficient of the yellow dye and the blue narrowband light, it is preferable to set the difference between the center wavelength of light transmitted through the B color filter and the center wavelength of the blue narrowband light to 50 nm or more and 100 nm or less.

Although the center wavelength of the B color filter is 450 nm in the present embodiment, this is a wavelength of an isosbestic point at which the absorption coefficient of oxygenated hemoglobin is almost equal to the absorption coefficient of reduced hemoglobin. Thus, by setting the center wavelength of light transmitted through the B color filter to a wavelength of the isosbestic point or a wavelength near the isosbestic point, it is possible to obtain the B2 image signal with low dependence on oxygen saturation while satisfying the condition that the absorption coefficient of blood hemoglobin is close to the blue narrowband light. Therefore, even if yellow dye is present, it is possible to calculate an accurate oxygen saturation by eliminating the influence of the yellow dye more strictly.

Figure 13:
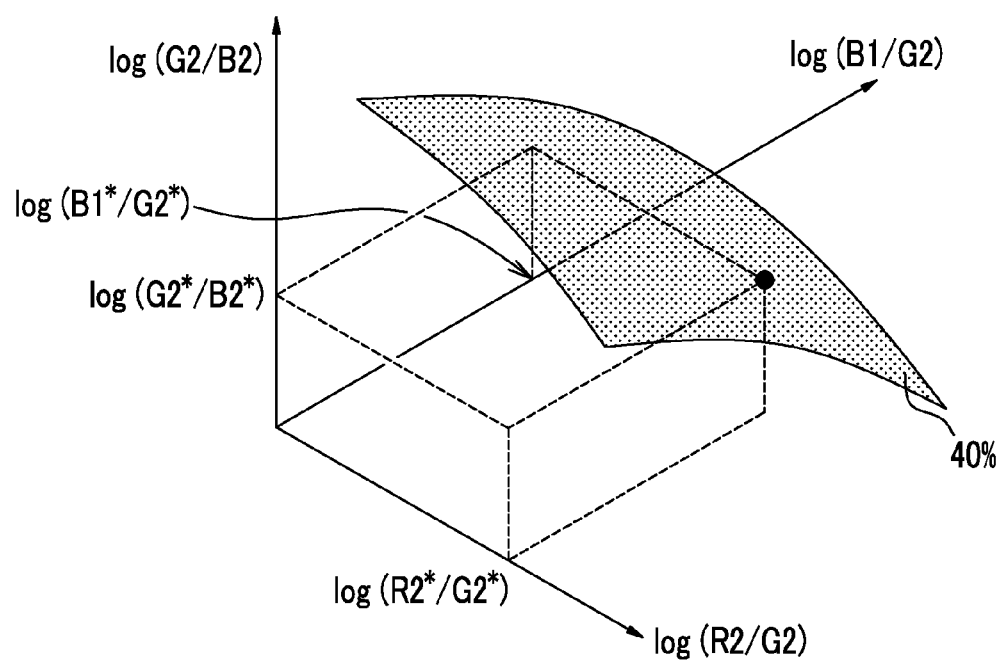
FIG. 13 is an explanatory diagram showing a method of calculating the oxygen saturation.

The oxygen saturation calculation section 83 calculates the oxygen saturation using the signal ratio calculated by the signal ratio calculation section 81. More specifically, the oxygen saturation calculation section 83 calculates the oxygen saturation corresponding to the signal ratio calculated by the signal ratio calculation section 81, for each pixel, with reference to the correlation table stored in the correlation storage section 82. For example, when the signal ratio B1/G2, the signal ratio R2/G2, and the signal ratio G2/B2 in a specific pixel are B1*/G2*, R2*/G2*, and G2*/B2*, respectively, the oxygen saturation corresponding to the signal ratio B1*/G2*, R2*/G2*, and G2*/B2* is "40%", as shown in FIG. 13, when the correlation table is referred to. Accordingly, the oxygen saturation calculation section 83 calculates the oxygen saturation of the specific pixel as "40%".

In addition, a case where the signal ratio B1/G2, the signal ratio R2/G2, and the signal ratio G2/B2 become extremely large or extremely small hardly occurs. That is, a case hardly occurs in which a combination of values of the signal ratio B1/G2, the signal ratio R2/G2, and the signal ratio G2/B2 exceeds a lower limit isosurface 93 (refer to FIG. 9) of the oxygen saturation of 0% or on the contrary becomes lower than an upper limit isosurface 94 (refer to FIG. 9) of the oxygen saturation of 100%. Here, the oxygen saturation calculation section 83 sets the oxygen saturation to 0% when the calculated oxygen saturation is lower than the lower limit isosurface 93, and sets the oxygen saturation to 100% when the calculated oxygen saturation exceeds the upper limit isosurface 94. When a point corresponding to the signal ratio B1/G2, the signal ratio R2/G2, and the signal ratio G2/B2 deviates from a region between the lower limit isosurface 93 and the upper limit isosurfaces 94, display showing that the reliability of the oxygen saturation in the pixel is low may be performed, or the oxygen saturation may not be calculated.

The image generation section 84 generates an oxygen saturation image by imaging the oxygen saturation using the oxygen saturation calculated by the oxygen saturation calculation section 83. Specifically, the image generation section 84 acquires a B2 image signal, a G2 image signal, and an R2 image signal, and multiplies these image signals by the gain corresponding to the oxygen saturation for each pixel. Then, RGB image data is generated using the B2 image signal, the G2 image signal, and the R2 image signal multiplied by the gain. For example, in a pixel where the corrected oxygen saturation is 60% or more, the image generation section 84 multiplies all of the B2 image signal, the G2 image signal, and the R2 image signal by the same gain "1". In contrast, in a pixel where the corrected oxygen saturation is less than 60%, the image generation section 84 multiplies the B2 image signal by the gain less than "1" and multiplies the G2 image signal and the R2 image signal by the gain of "1" or more. RGB image data generated using the B2 image signal, the G2 image signal, and the R2 image signal after the gain processing is the oxygen saturation image.

In the oxygen saturation image generated by the image generation section 84, a high oxygen region (region having an oxygen saturation of 60% to 100%) is expressed in the same color as the normal observation image. On the other hand, a low oxygen region where the oxygen saturation is less than a specific value (region having an oxygen saturation of 0% to 60%) is expressed in a different color (pseudo color) from the normal observation image.

Although the image generation section 84 performs gain multiplication for pseudo coloring only for the low oxygen region in the present embodiment, a gain corresponding to the oxygen saturation may also be multiplied for the high oxygen region so that the entire oxygen saturation image is pseudo-colored. In addition, although the low oxygen region and the high oxygen region are divided at the oxygen saturation of 60%, this boundary can be arbitrarily selected.

Figure 14:
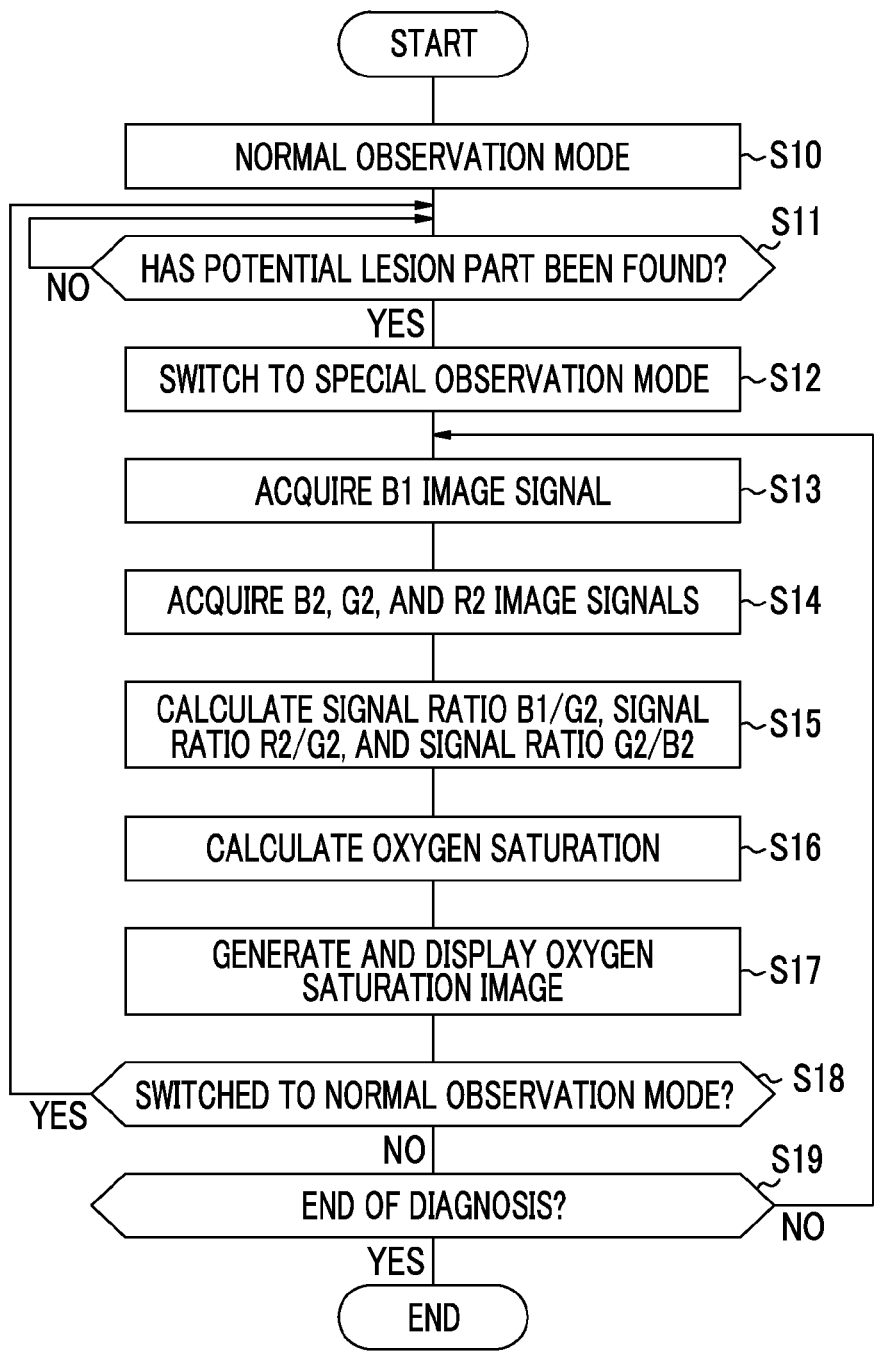
FIG. 14 is a flowchart showing the operation of the endoscope system.

Next, the flow of observation using the endoscope system 10 according to the present embodiment will be described with reference to the flowchart in FIG. 14. First, in the normal observation mode, screening is performed from the most distant view state (S10). In the normal observation mode, a normal observation image is displayed on the monitor 18. When a part that is likely to be a lesion (hereinafter, referred to as a potential lesion part), such as a brownish area or rubor, is found in this screening (S11), the mode selector SW 22b is operated for switching to the special observation mode (S12). Then, in the special observation mode, the potential lesion part is diagnosed.

In the special observation mode, the blue narrowband light and the white light are alternately emitted to the observation target in synchronization with the imaging frame of the sensor 48. Accordingly, the sensor 48 outputs the B1 image signal in the first frame, and outputs the R2 image signal, the G2 image signal, and the B2 image signal in the second frame. Then, in the processor device 16, when these imaging signals are acquired by the image signal acquisition unit 54 (S13 and S14: image signal acquisition step), the signal ratio calculation section 81 calculates the signal ratio B1/G2, the signal ratio R2/G2, and the signal ratio G2/B2 (S15). Based on these signal ratios, the oxygen saturation calculation section 83 calculates the oxygen saturation for each pixel (S16: oxygen saturation calculation step). Then, the image generation section 84 generates an oxygen saturation image based on the image signals B2, G2, and R2 and the oxygen saturation calculated by the oxygen saturation calculation section 83 (S17: oxygen saturation image generation step). In addition, these operations are repeatedly performed until the switching to the normal observation mode (S17) or until the end of diagnosis (S18).

Figure 15:
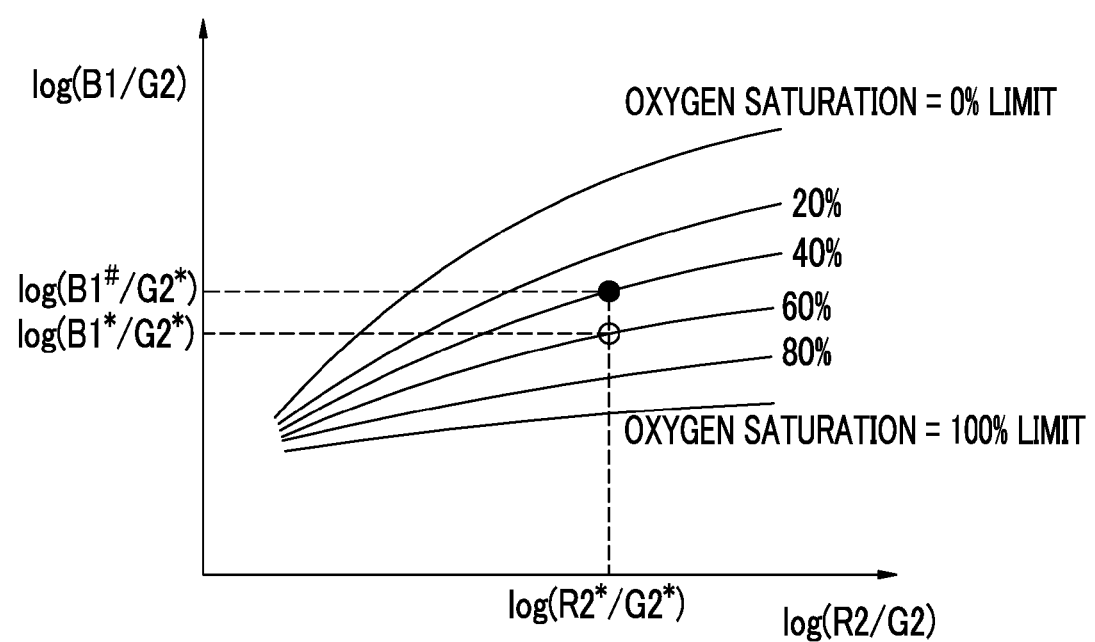
FIG. 15 is a graph showing a correlation and the oxygen saturation calculation accuracy in a comparative example.

As shown in FIG. 15, when calculating the oxygen saturation using a two-dimensional correlation table that maps the signal ratio B1/G2 and the signal ratio R2/G2 with the oxygen saturation without using the signal ratio G2/B2, an error occurs in the oxygen saturation if the observation target is contaminated with mucus containing yellow dye or the like. For example, when the signal values of image signals in a specific pixel are B1*, R2*, G2*, and B2*, the oxygen saturation calculated by using a two-dimensional correlation table is assumed to be "60%". Unless mucus containing yellow dye or the like adheres to the observation target, this value indicates the oxygen saturation of the observation target. However, if mucus containing yellow dye or the like adheres to the observation target, there is light absorption not only by blood hemoglobin but also by the yellow dye. The measured signal values B1*, R2*, G2*, and B2* are signal values reflecting the light absorption of blood hemoglobin and the light absorption of the yellow dye. The yellow dye absorbs a large amount of light in the blue wavelength band in particular (refer to FIG. 12). Therefore, assuming that there is light absorption of the yellow dye only in the blue wavelength band for simplicity, the signal values B1* and B2* are smaller than true signal values $B1^{\#}$ and $B2^{\#}$ obtained by imaging the observation target when there is no yellow dye. That is, the relationship of $B1^*<B1^{\#}$ and $B2^*<B2^{\#}$ is satisfied. In this case, "40%" corresponding to the signal ratio $B1^{\#}/G2^*$ and the signal ratio $R2^*/G2^*$ is the true oxygen saturation of the observation target in the specific pixel. For this reason, when mucus containing yellow dye or the like adheres to the observation target, the oxygen saturation "60%" calculated based on the signal ratio B1*/G2* and the signal ratio R2*/G2* is higher than the true oxygen saturation "40%" of the observation target.

On the other hand, in the endoscope system 10, the oxygen saturation is calculated by using not only the signal ratio B1/G2 and the signal ratio R2/G2 but also the signal ratio G2/B2 using the three-dimensional correlation table (refer to FIG. 9) that maps the three signal ratios with the oxygen saturation. Thus, the endoscope system 10 can calculate the true oxygen saturation "40%" of the observation target using the signal values B1*, R2*, G2*, and B2* of image signals obtained when the observation target is contaminated with mucus containing yellow dye or the like.

Figure 16:
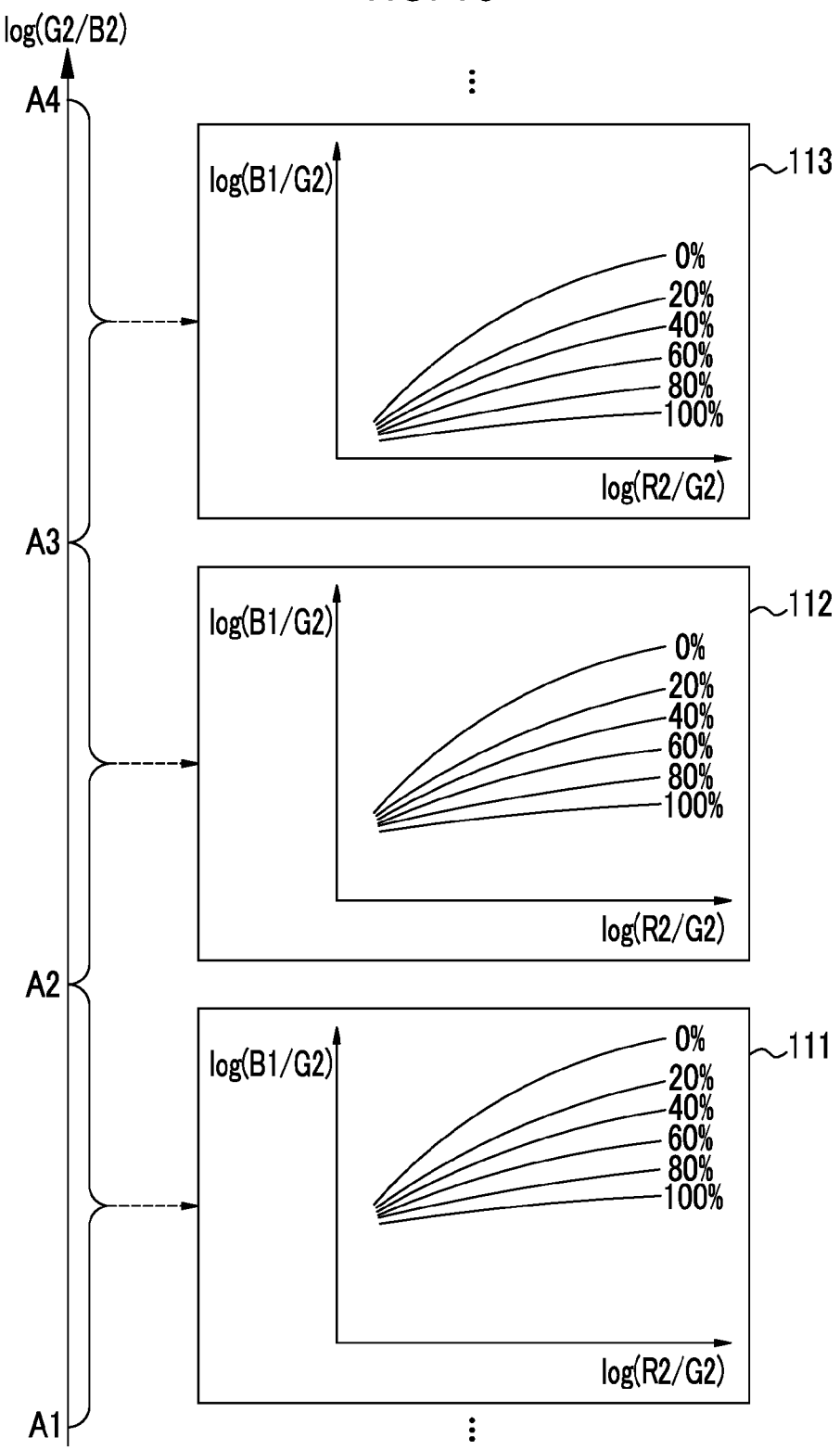
FIG. 16 is an explanatory diagram of a modification example in which a plurality of two-dimensional correlations according to the signal ratio G2/B2 are used.

In the first embodiment, the three-dimensional correlation table that maps the signal ratio B1/G2, the signal ratio R2/G2, and the signal ratio G2/B2 with the oxygen saturation is used. Instead, a plurality of two-dimensional correlation tables that map the signal ratio B1/G2 and the signal ratio R2/G2 with the oxygen saturation may be prepared according to the signal ratio G2/B2, and the oxygen saturation may be calculated using the correlation corresponding to the signal ratio G2/B2 in the plurality of two-dimensional correlation tables. For example, as shown in FIG. 16, a two-dimensional correlation table 111 that is used when the value of log(G2/B2) is equal to or greater than A1 and less than A2, a two-dimensional correlation table 112 that is used when the value of log(G2/B2) is equal to or greater than A2 and less than A3, and a two-dimensional correlation table 113 that is used when the value of log(G2/B2) is equal to or greater than A3 and less than A4 may be prepared, and the oxygen saturation may be calculated by selecting and using the corresponding two-dimensional correlation according to the value of log(G2/B2).

Second Embodiment

Figure 17:
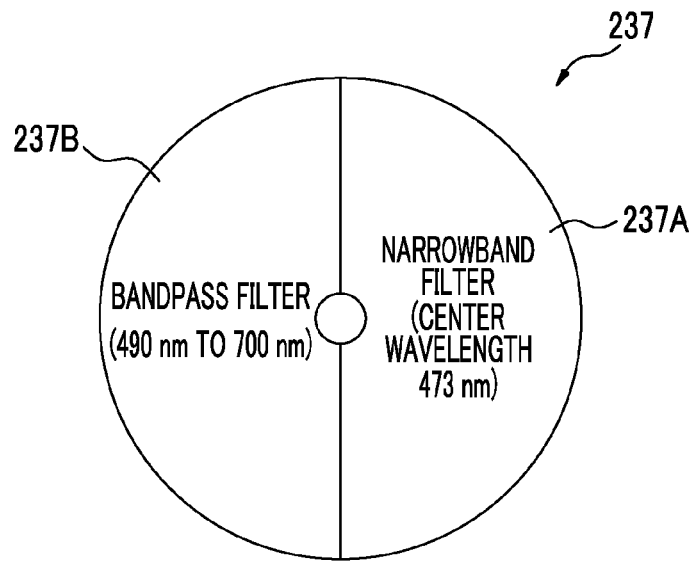
FIG. 17 is a rotary filter in a second embodiment.

In an endoscope system according to a second embodiment, a rotary filter 237 shown in FIG. 17 is used instead of the rotary filter 37 of the first embodiment. Other configurations are the same as the endoscope system 10 according to the first embodiment.

The rotary filter 237 includes a narrowband filter 237A and a band pass filter 237B. The narrowband filter 237A transmits blue narrowband light having a center wavelength of 473±10 nm. That is, the narrowband filter 237A is the same as the narrowband filter 37A of the rotary filter 37 in the first embodiment. On the other hand, the band pass filter 237B is provided instead of the opening 37B of the rotary filter 37 in the first embodiment, and transmits light in a wavelength band of 490 nm or more and 700 nm or less and cuts light in other wavelength bands. The rotary filter 237 is provided so as to be retractable from the optical path of the white light, and is retracted from the optical path of the white light in the normal observation mode.

Figure 18:
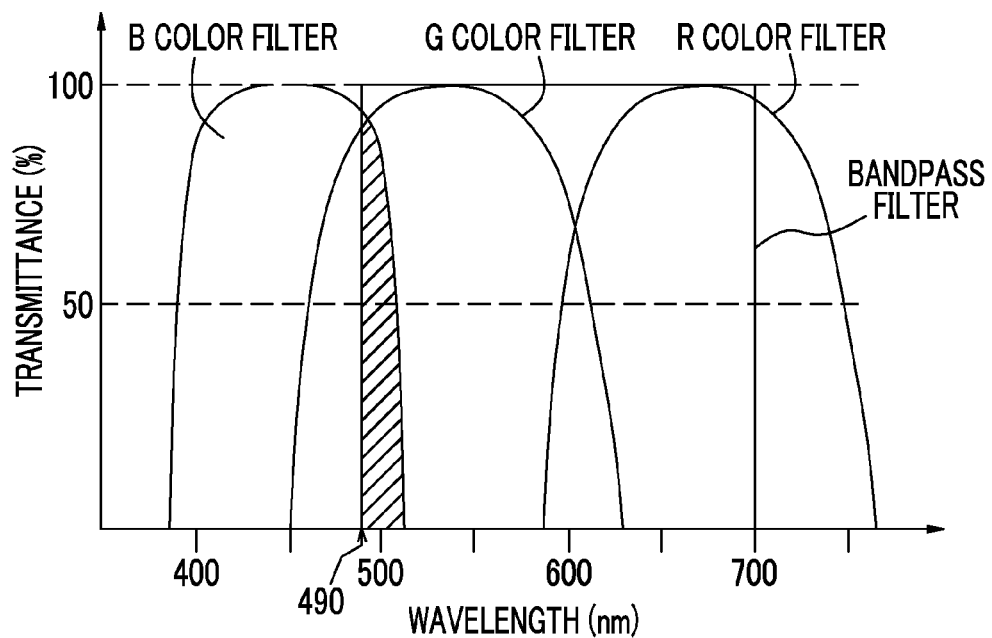
FIG. 18 is a graph showing the operation in the second embodiment.

When the rotary filter 237 is used, light emitted to the observation target in the second frame in the special observation mode is white light limited to the light in a wavelength band of 490 nm or more and 700 nm or less that is transmitted through the band pass filter 237B. On the other hand, since the transmission wavelength band of the B color filter is 390 nm to 510 nm, the wavelength band of light incident on the B pixel in the second frame in the special observation mode is 500±10 nm, as shown in FIG. 18. This wavelength band is an isosbestic point at which the absorption coefficient of oxygenated hemoglobin is almost equal to the absorption coefficient of reduced hemoglobin (refer to FIG. 11). Accordingly, when the rotary filter 237 is used, the dependence of the B2 image signal on the oxygen saturation is reduced, and the signal ratio G2/B2 becomes a more accurate value corresponding to the amount of light absorption of the yellow dye. Therefore, by setting the B2 image signal as an image signal corresponding to the narrowband light near the isosbestic point using the rotary filter 237, it is possible to calculate the oxygen saturation more accurately than in the endoscope system 10 according to the first embodiment.

Third Embodiment

Figure 19:
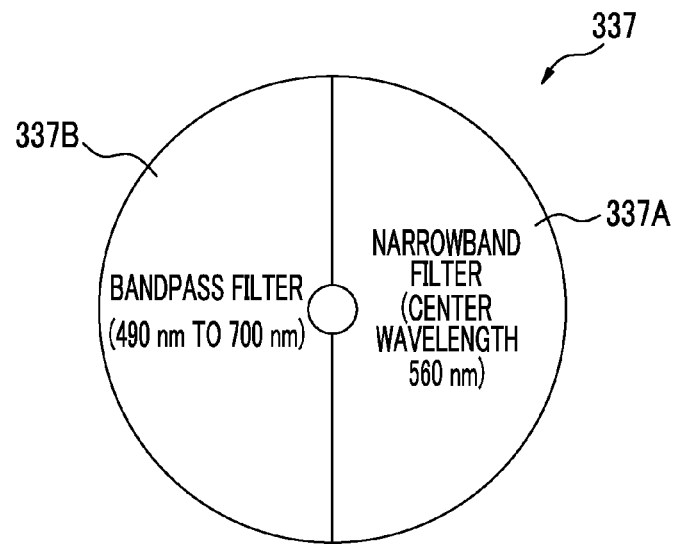
FIG. 19 is a rotary filter in a third embodiment.

In an endoscope system according to a third embodiment, a rotary filter 337 shown in FIG. 19 is used instead of the rotary filter 37 of the first embodiment. The rotary filter 337 includes a narrowband filter 337A and a band pass filter 337B. The narrowband filter 337A transmits green narrowband light having a center wavelength of 560±5 nm, and cuts light in other wavelength bands. The wavelength band of the green narrowband light is a wavelength band where the difference between the absorption coefficient of oxygenated hemoglobin and the absorption coefficient of reduced hemoglobin is large, as for the blue narrowband light (473±10 nm) (refer to FIG. 11). Therefore, in the case of the green narrowband light, the amount of light absorption changes according to the oxygen saturation of blood hemoglobin. The band pass filter 337B transmits light in a wavelength band of 490 nm or more and 700 nm or less, and cuts light in other wavelength bands. That is, the band pass filter 337B is the same as the band pass filter 237B of the rotary filter 237 in the second embodiment. The rotary filter 337 is provided so as to be retractable from the optical path of the white light, and is retracted from the optical path of the white light in the normal observation mode.

Figure 20:
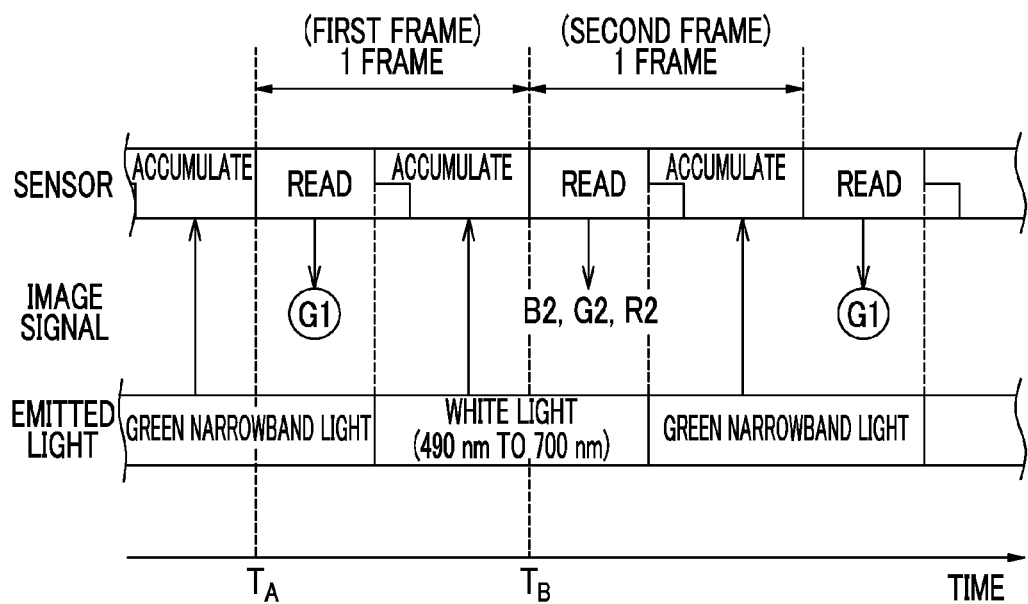
FIG. 20 is an explanatory diagram showing imaging control in a third embodiment.

As shown in FIG. 20, when the rotary filter 337 is used, light emitted to the observation target in the first frame in the special observation mode is green narrowband light, and light emitted to the observation target in the second frame in the special observation mode is white light in a wavelength band of 490 nm or more and 700 nm or less that is transmitted through the band pass filter 337B. Accordingly, in the first frame, a G1 image signal output from the G pixel is acquired instead of the B1 image signal.

The signal ratio calculation section 81 calculates the signal ratio G1/G2 instead of the signal ratio B1/G2, and the oxygen saturation calculation section 83 calculates the oxygen saturation based on the signal ratio G1/G2, the signal ratio R2/G2, and the signal ratio G2/B2. Therefore, as shown in FIG. 21, a three-dimensional correlation table that maps the signal ratio G1/G2, the signal ratio R2/G2, and the signal ratio G2/B2 with the oxygen saturation is stored in the correlation storage section 82.

In this manner, it is possible to calculate the oxygen saturation using the green narrowband light instead of the blue narrowband light. In addition, the endoscope system according to the third embodiment calculates the oxygen saturation in consideration of the signal ratio G2/B2. Accordingly, even if the observation target is contaminated with mucus containing yellow dye or the like, it is possible to calculate an accurate oxygen saturation in the same manner as the endoscope system 10 according to the first embodiment.

Figure 9:
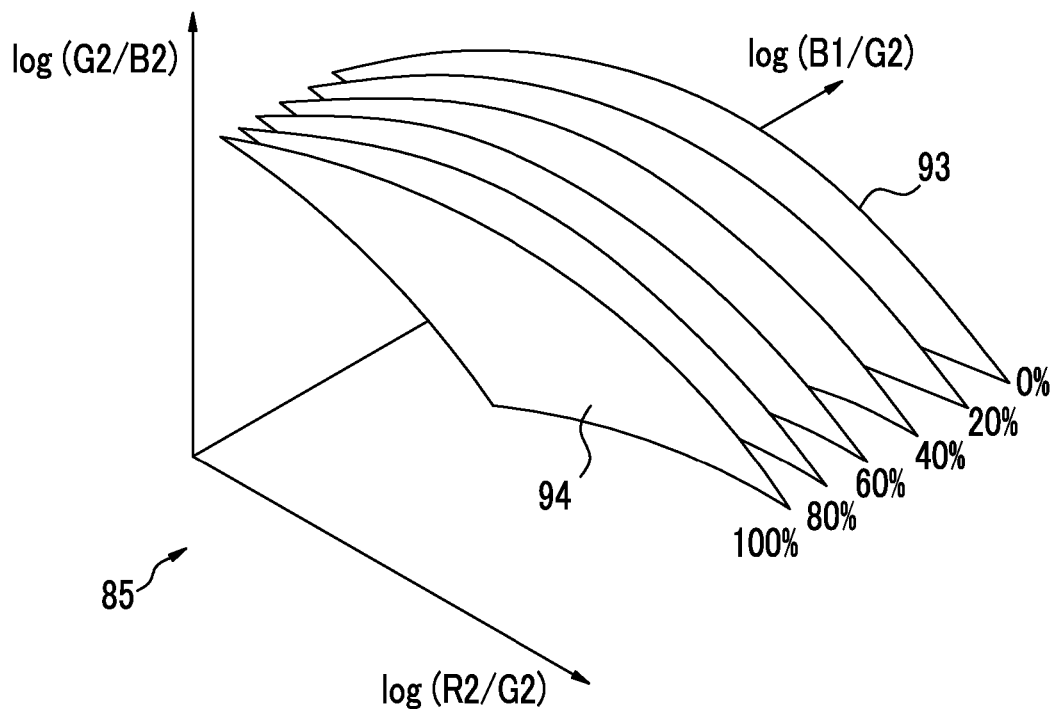
FIG. 9 is an explanatory diagram showing a correlation table between a signal ratio and oxygen saturation.
Figure 10:
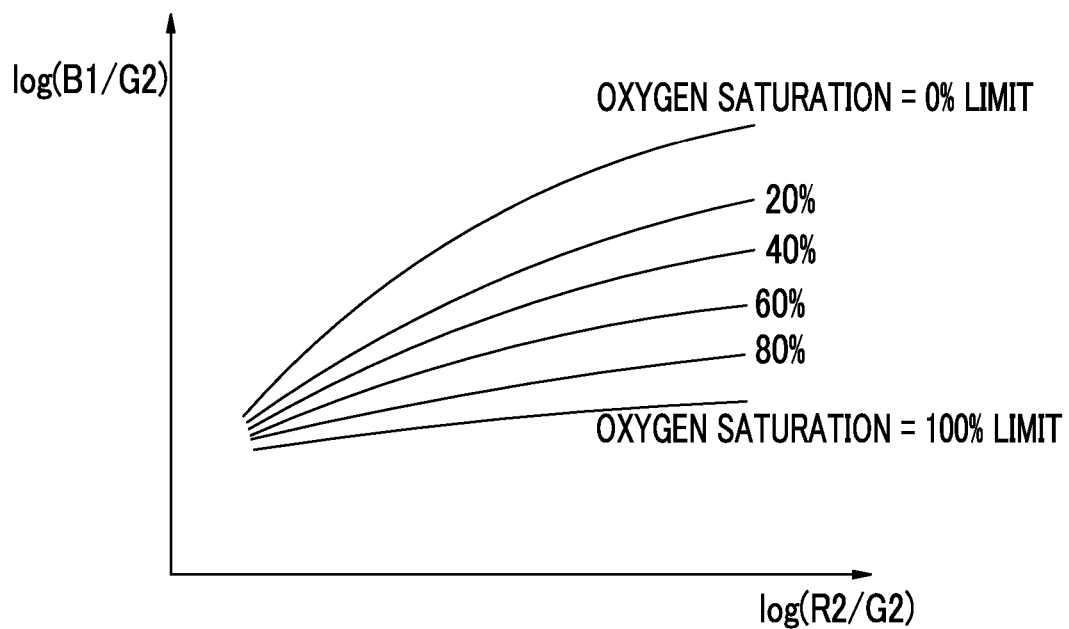
FIG. 10 is a graph showing the cross-section of isosurfaces when a signal ratio G2/B2 is an arbitrary value.
Figure 21:
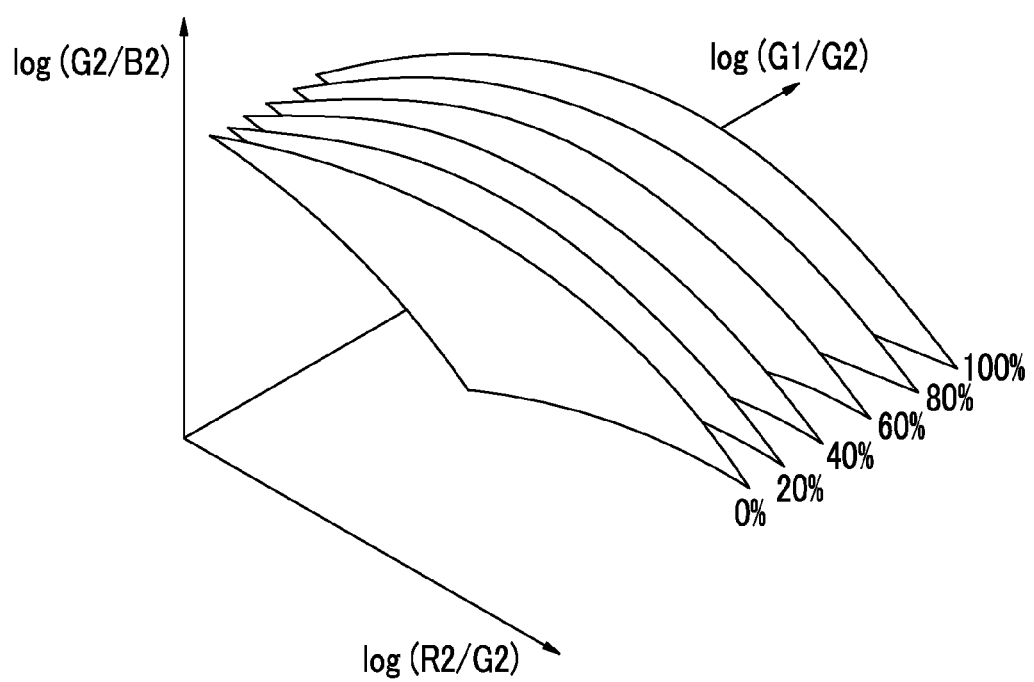
FIG. 21 is a correlation table between a signal ratio and oxygen saturation that is used in the third embodiment.

The reason why the sequence of isosurfaces of oxygen saturation in the correlation table of FIG. 21 is reversed with respect to the correlation table of FIG. 9 is that the absorption coefficient of oxygenated hemoglobin exceeds the absorption coefficient of reduced hemoglobin in the wavelength band of blue narrowband light while the absorption coefficient of reduced hemoglobin exceeds the absorption coefficient of oxygenated hemoglobin in the wavelength band of green narrowband light.

In the third embodiment, the same band pass filter 337B as in the second embodiment is used in the rotary filter 337. However, it is also possible to use an opening instead of the band pass filter 337B as in the first embodiment.

When calculating the oxygen saturation based on the signal ratio G1/G2 as in the third embodiment, it is preferable that both the center wavelength of the wavelength band corresponding to the G1 image signal and the center wavelength of the wavelength band corresponding to the G2 image signal are in the wavelength band of 450 nm or more and 650 nm or less. In contrast, when calculating the oxygen saturation based on the signal ratio B1/G2 as in the first embodiment, it is preferable that the center wavelength of the wavelength band corresponding to the B1 image signal and the center wavelength of the wavelength band corresponding to the G2 image signal are in the wavelength band of 350 nm or more and 500 nm or less. This is to improve the accuracy of oxygen saturation to be calculated by setting the absorption coefficient of blood hemoglobin and the scattering coefficient by the observation target to close values.

Fourth Embodiment

Figure 22:
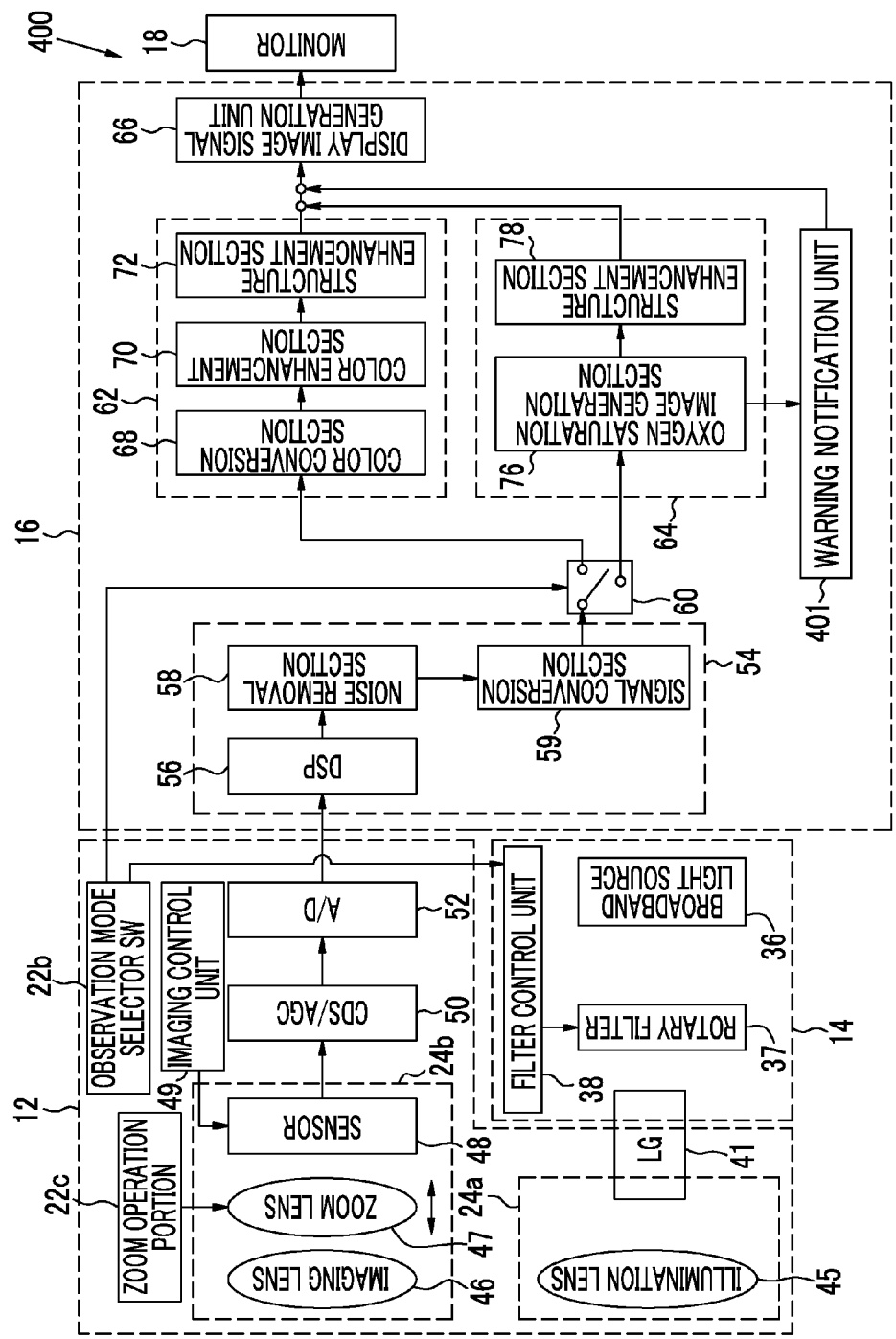
FIG. 22 is a block diagram of an endoscope system according to a fourth embodiment.

As shown in FIG. 22, an endoscope system 400 according to a fourth embodiment is formed by providing a warning notification unit 401 in the processor device 16 in the endoscope system 10 according to the first embodiment. Other configurations are the same as the endoscope system 10 according to the first embodiment.

The warning notification unit 401 acquires the signal ratio G2/B2 from the signal ratio calculation section 81 of the oxygen saturation image generation section 76 and compares the signal ratio G2/B2 with a threshold value $Q_{TH}$. When there is a pixel having the signal ratio G2/B2 equal to or greater than the threshold value $Q_{TH}$, the warning notification unit 401 generates a warning signal. That is, the warning signal is generated when the signal ratio G2/B2 is large and the observation target is severely contaminated with mucus containing yellow dye. The warning signal is input to the display image signal generation unit 66. This is an example of determining whether or not the third signal ratio is a value in a specific range using the threshold value $Q_{TH}$.

Figure 23:
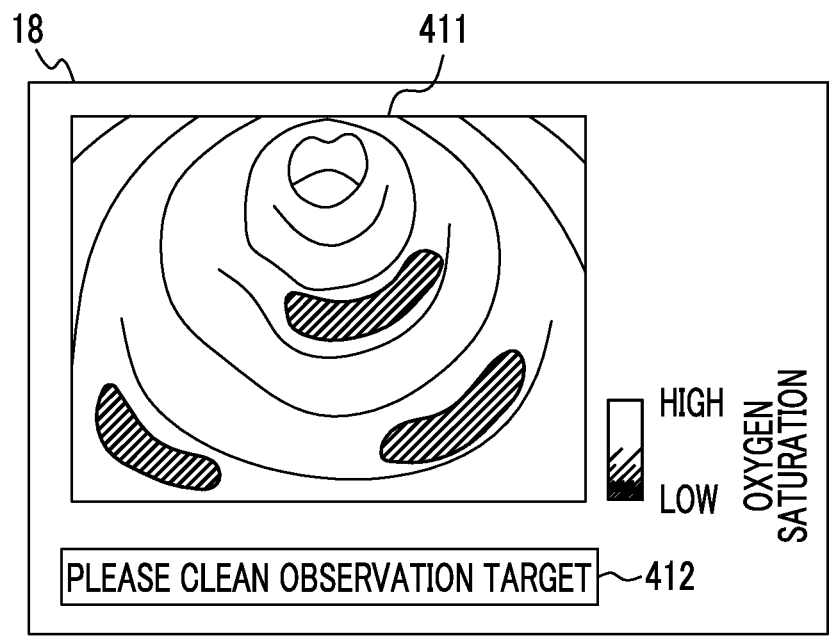
FIG. 23 is an explanatory diagram showing the operation in the fourth embodiment.

As shown in FIG. 23, when the warning signal is input, the display image signal generation unit 66 displays a warning message 412 prompting the cleaning of the observation target on the monitor 18 together with an oxygen saturation image 411. Since the endoscope system 400 calculates the oxygen saturation based on not only the signal ratio B1/G2 and the signal ratio R2/G2 but also the signal ratio G2/B2, it is possible to calculate an accurate oxygen saturation even if mucus containing yellow dye or the like adheres to the observation target. However, when the observation target is contaminated too much, an error may be large even if the oxygen saturation is calculated based on the signal ratio G2/B2. Accordingly, if the warning message 412 is displayed to notify of the need for cleaning as described above, a doctor who uses the endoscope system 400 can accurately grasp the severity of dirt adhering to the observation target when performing diagnosis based on the oxygen saturation of the observation target. In addition, when the warning message 412 is displayed, it is possible to perform diagnosis based on the oxygen saturation after cleaning the observation target. Therefore, more accurate diagnosis can be performed.

Figure 24:
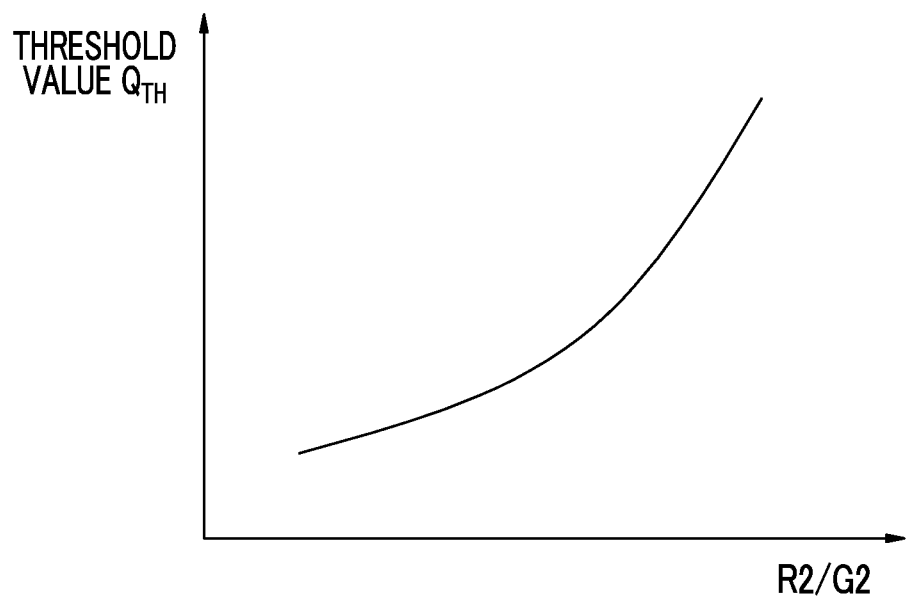
FIG. 24 is a graph showing the relationship between a threshold value and the signal ratio R2/G2.

The warning notification unit 401 acquires the signal ratio R2/G2 from the signal ratio calculation section 81, and changes the threshold value $Q_{TH}$ for comparison with the signal ratio G2/B2 according to the signal ratio R2/G2, for example, as shown in FIG. 24. That is, the warning notification unit 401 changes the threshold value $Q_{TH}$ according to the blood volume of the observation target. This is because the distance between isosurfaces of oxygen saturation in the correlation table changes according to the signal ratio R2/G2 (refer to FIGS. 9 and 10). For example, even if the signal ratio G2/B2 reflecting the amount of yellow dye is a fixed value, when the signal ratio R2/G2 is small and the blood volume is small, the distance between isosurfaces of oxygen saturation is small. Even if the signal ratio G2/B2 deviates slightly, the error of the oxygen saturation calculated is large. Therefore, if the threshold value $Q_{TH}$ is changed according to the blood volume, it is possible to appropriately determine the magnitude of the influence of the amount of yellow dye on the calculation of oxygen saturation and give a warning for prompting the cleaning.

The warning notification unit 401 may acquire the signal ratio B1/G2 from the signal ratio calculation section 81, and change the threshold value $Q_{TH}$ according to the signal ratio B1/G2. If the threshold value $Q_{TH}$ is changed according to the signal ratio B1/G2 as described above, the dependence of the threshold value $Q_{TH}$ on the oxygen saturation can be reduced. Therefore, compared with a case where the fixed threshold value $Q_{TH}$ is used, it is possible to appropriately determine the magnitude of the influence of the amount of yellow dye on the calculation of oxygen saturation and give a warning for prompting the cleaning. In addition, if the warning notification unit 401 is made to acquire the signal ratio R2/G2 and the signal ratio B1/G2 from the signal ratio calculation section 81 and change the threshold value $Q_{TH}$ according to these signal ratios, it is possible to reduce the dependence of the threshold value $Q_{TH}$ on the blood volume and the oxygen saturation. Therefore, it is possible to appropriately determine the magnitude of the influence of the amount of yellow dye on the calculation of oxygen saturation and give a warning for prompting the cleaning.

In the endoscope system 400 according to the fourth embodiment, the warning message 412 is displayed on the monitor 18. Instead, it is also possible to prompt the cleaning of the observation target by outputting a warning sound, reproducing a warning message by voice, or turning on a lamp or a rotation lamp.

Figure 25:
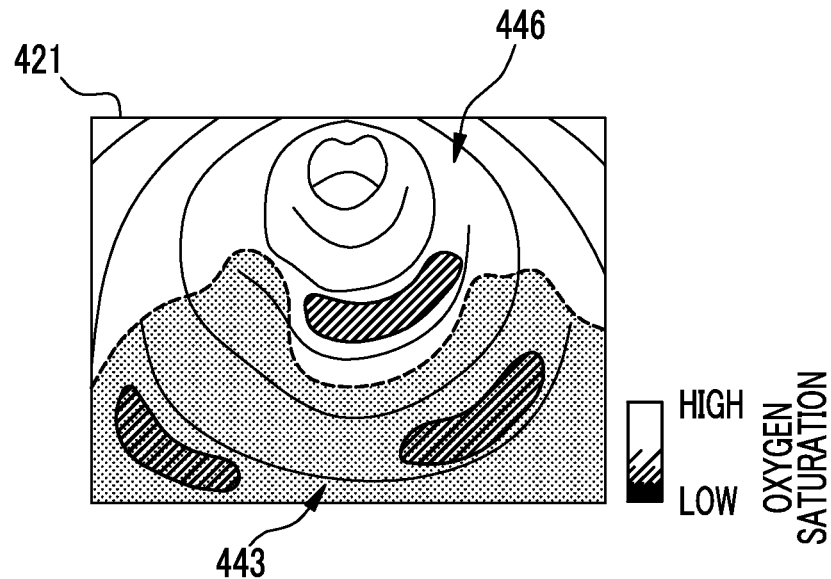
FIG. 25 is an explanatory diagram showing the operation in a modification example of the fourth embodiment.

The warning notification unit 401 may detect a region where there is a pixel having the signal ratio G2/B2 equal to or greater than the threshold value $Q_{TH}$ and output a warning signal as position information of the pixel having the signal ratio G2/B2 equal to or greater than the threshold value $Q_{TH}$. In this case, for example, when converting the oxygen saturation image that is RGB image data into the brightness signal Y and the color difference signals Cb and Cr for display on the monitor 18, the display image signal generation unit 66 replaces the color difference signals Cb and Cr of the pixel having the signal ratio G2/B2 equal to or greater than the threshold value $Q_{TH}$ with zero. As a result, for example, as shown in FIG. 25, an oxygen saturation image 421 is displayed on the monitor 18. The oxygen saturation image 421 is divided into a contaminated region 443 where the signal ratio G2/B2 is equal to or greater than the threshold value $Q_{TH}$ and a clean region 446 where the signal ratio G2/B2 is less than the threshold value $Q_{TH}$. In the oxygen saturation image 421, the contaminated region 443 is displayed in an achromatic color, and the clean region 446 is displayed in a chromatic color that is pseudo-colored according to the oxygen saturation. Thus, by displaying differently a pixel having the signal ratio G2/B2 in a specific range and a pixel having the signal ratio G2/B2 outside the specific range, it is possible to determine a region where the error of oxygen saturation is large due to mucus containing yellow dye. By observing the position or area of the contaminated region 443, it is possible to determine the need for cleaning. This replaces the warning message 412.

In this example, the color difference signals Cb and Cr of all pixels having the signal ratio G2/B2 equal to or greater than the threshold value $Q_{TH}$ are replaced with zero. However, the color difference signals Cb and Cr of only a pixel that has the signal ratio G2/B2 equal to or greater than the threshold value $Q_{TH}$ and has a pseudo-colored value (for example, less than 60%) of oxygen saturation may be replaced with zero so that the pixel is displayed in an achromatic color. In addition, although color adjustment is performed in a stage of generating the display image signal, the display color of the pixel having the signal ratio G2/B2 equal to or greater than the threshold value $Q_{TH}$ may be changed in a stage of generating the oxygen saturation image. In this case, the image generation section 84 performs this processing in response to a warning signal.

In the first to fourth embodiments, the broadband light source 36 is used. Instead of the broadband light source 36, it is also possible to use a light source that generates white light with LEDs of RGB or a light source that generates white light with a laser diode (LD) and a phosphor that is excited by laser light emitted from the LD and emits light. In the case of using these light source devices, the rotary filters 37, 237, and/or 337 may be used together as in the embodiments described above, or the wavelength band of illumination light or the amount of illumination light may be adjusted by ON/OFF of the LEDs or the LD or by distribution adjustment of the amount of light instead of the rotary filters 37, 237, and/or 337.

Figure 26:
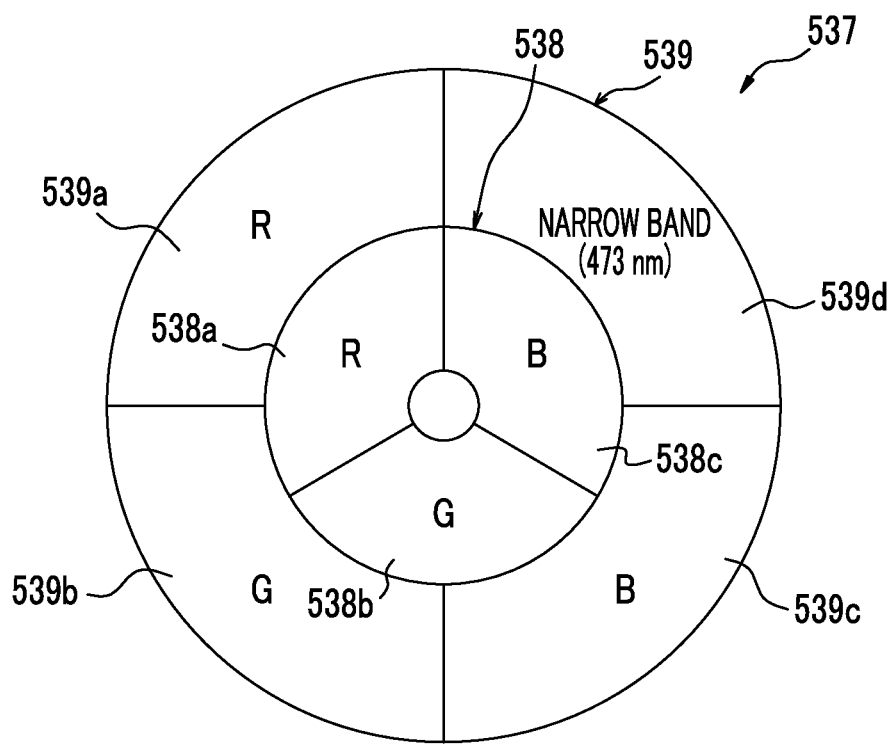
FIG. 26 is a rotary filter used in the case of using a monochrome imaging device.

Although the color imaging device in which RGB color filters are provided is used as the sensor 48 in the first to fourth embodiments, a monochrome imaging device in which no color filter is provided may be used as the sensor 48. In this case, a rotary filter 537 shown in FIG. 26 is used.

The rotary filter 537 includes a normal observation mode filter 538 and a special observation mode filter 539, and is provided so as to be movable between a first position to place the normal observation mode filter 538 on the optical path of the white light and a second position to place the special observation mode filter 539 on the optical path of the white light. The normal observation mode filter 538 is provided in the inner peripheral portion of the rotary filter 537, and includes an R filter 538a that transmits red light, a G filter 538b that transmits green light, and a B filter 538c that transmits blue light. Therefore, when the rotary filter 537 is placed at the first position for normal observation mode, the white light from the broadband light source 36 is incident on one of the R filter 538a, the G filter 538b, and the B filter 538c according to the rotation of the rotary filter 537. As a result, red light, green light, and blue light are sequentially emitted to the observation target according to the transmitted filter, and the monochrome sensor outputs sequentially an R image signal, a G image signal, and a B image signal by imaging the observation target with reflected light of the red light, the green light, and the blue light.

The special observation mode filter 539 is provided in the outer peripheral portion of the rotary filter 537. The special observation mode filter 539 includes an R filter 539a that transmits red light, a G filter 539b that transmits green light, a B filter 539c that transmits blue light, and a narrowband filter 539d that transmit narrowband light of 473±10 nm. Therefore, when the rotary filter 537 is placed at the second position for special observation mode, the white light from the broadband light source 36 is incident on one of the R filter 539a, the G filter 539b, the B filter 539c, and the narrowband filter 539d according to the rotation of the rotary filter 537. As a result, red light, green light, blue light, and narrowband light (473 nm) are sequentially emitted to the observation target according to the transmitted filter, and the monochrome sensor outputs sequentially an R image signal, a G image signal, a B image signal, and a narrowband image signal by imaging the observation target with reflected light of the red light, the green light, the blue light, and the narrowband light.

RGB image signals acquired in the special observation mode correspond to the R2 image signal, the G2 image signal, and the B2 image signal in the first embodiment, respectively. The narrowband image signal acquired in the special observation mode corresponds to the B1 image signal in the first embodiment. Accordingly, subsequent processing can be performed in the same manner as in the endoscope system 10 according to the first embodiment.

Although the oxygen saturation is calculated based on the signal ratio B1/G2, the signal ratio R2/G2, and the signal ratio G2/B2 in the first to fourth embodiments, the oxygen saturation may be calculated based on only the signal ratio B1/G2 and the signal ratio G2/B2. In this case, it is preferable to store the correlation between the signal ratio B1/G2 and the signal ratio G2/B2 and the oxygen saturation in the correlation storage section 82.

Although the oxygen saturation image obtained by imaging the oxygen saturation is generated and displayed in the first to sixth embodiments, a blood volume image obtained by imaging the blood volume may be generated and displayed in addition to the generation and display of the oxygen saturation image. Since the blood volume is correlated with the signal ratio R2/G2, a blood volume image obtained by imaging the blood volume can be generated by assigning different colors according to the signal ratio R2/G2.

In the first to fourth embodiments, the oxygen saturation is calculated. However, instead of or in addition to the oxygen saturation, other biological function information, such as an oxygenated hemoglobin index that is calculated from "blood volume×oxygen saturation (%)" or a reduced hemoglobin index that is calculated from "blood volume× (1−oxygen saturation) (%)", may be calculated.

Figure 27:
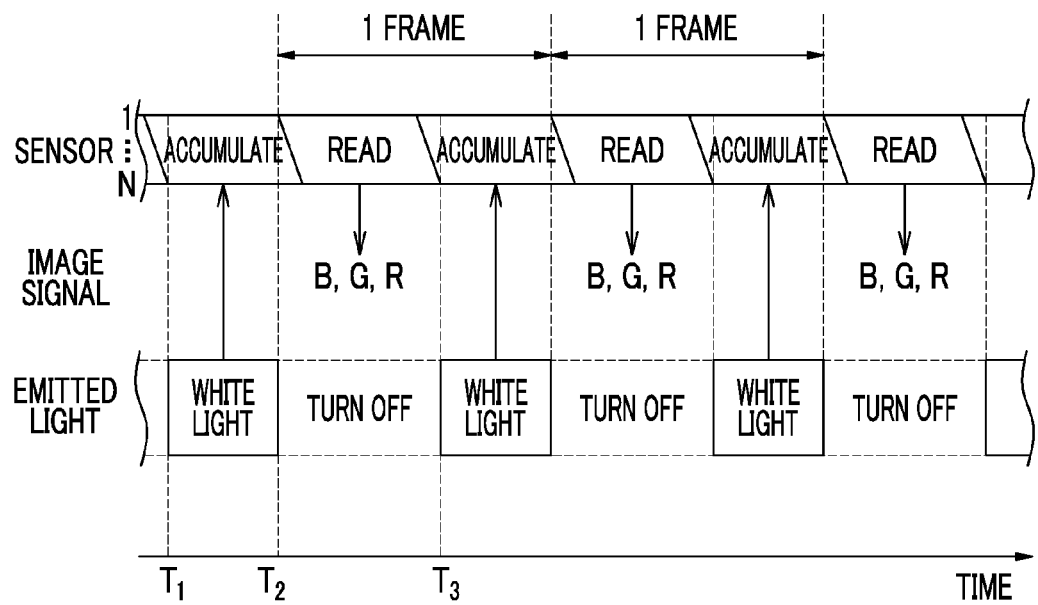
FIG. 27 is an explanatory view showing imaging control in the normal observation mode in the case of using a CMOS image sensor.
Figure 28:
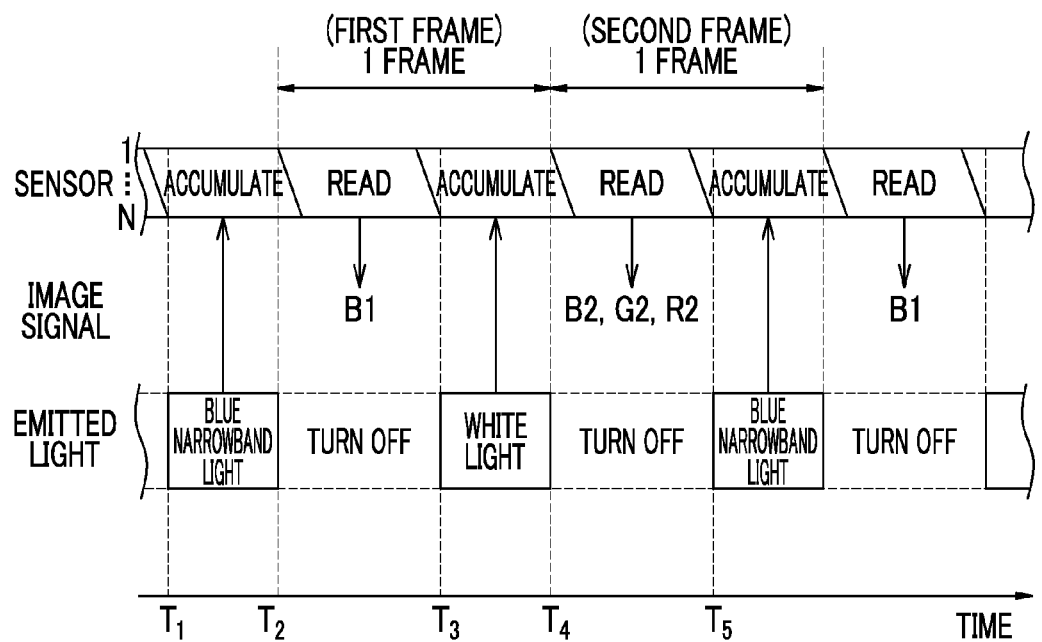
FIG. 28 is an explanatory view showing imaging control in the special observation mode in the case of using a CMOS image sensor.

Although the CCD image sensor is used as the sensor 48 in the first to fourth embodiments, a CMOS image sensor may also be used as the sensor 48. In this case, the CMOS image sensor is driven in a so-called rolling shutter method, and accumulation and reading of the signal charge are sequentially performed for each row (each of first to N-th rows) of pixels. For this reason, the timing of the accumulation and reading of the signal charge of each row differs according to each row. Therefore, switching between the blue narrowband light (or the green narrowband light) and the white light is preferably performed in accordance with the reading timing. For example, as shown in FIG. 27, in the normal observation mode, the emission of the white light is performed until the accumulation of the first row is completed (time $T_2$) from the start of the accumulation of the N-th row (time $T_1$), while the emission of the white light is stopped until the reading of the N-th row is completed (time $T_3$) from the start of the reading of the first row (time $T_2$). In addition, as shown in FIG. 28, in the special observation mode, the emission of the blue narrowband light is performed until the accumulation of the first row is completed (time $T_2$) from the start of the accumulation of the N-th row (time $T_1$), while the emission of the blue narrowband light and the white light is stopped until the reading of the N-th row is completed (time $T_3$) from the start of the reading of the first row (time $T_2$). Then, in the next frame, the emission of the white light is performed until the accumulation of the first row is completed (time $T_4$) from the start of the accumulation of the N-th row (time $T_3$), while the emission of the blue narrowband light and the white light is stopped until the reading of the N-th row is completed (time $T_5$) from the start of the reading of the first row (time $T_4$). Thus, it is possible to standardize the length (exposure) of the substantial charge accumulation period of each row and to prevent the signal based on the blue narrowband light and the signal based on the white light from being mixed. Therefore, even when a CMOS image sensor is used as the sensor 48, it is possible to calculate an accurate oxygen saturation as in the embodiments described above.

What is claimed is:

1. An endoscope system, comprising:
a processor device configured to:
acquire a first image signal corresponding to a first wavelength band where an amount of light absorption changes according to oxygen saturation of blood hemoglobin, a second image signal corresponding to a second wavelength band where the amount of light absorption changes according to a blood volume of an observation target, a third image signal corresponding to a third wavelength band where a change in the amount of light absorption with respect to the oxygen saturation is small compared with the first image signal and a change in the amount of light absorption with respect to the blood volume is small compared with the second image signal, and a fourth image signal corresponding to a fourth wavelength band, a difference between a center wavelength of the first wavelength band and a center wavelength of the fourth wavelength band being 20 nm or more and 100 nm or less,
calculate oxygen saturation of the observation target for each pixel based on the first image signal, the second image signal, the third image signal, and the fourth image signal, and
calculate, for each pixel, a first signal ratio that is a ratio of the first image signal to the second image signal, a second signal ratio that is a ratio of the third image signal to the second image signal, and a third signal ratio that is a ratio of the second image signal to the fourth image signal,
wherein the processor device calculates the oxygen saturation based on the first signal ratio, the second signal ratio, and the third signal ratio.

2. The endoscope system according to claim 1, further comprising:
a correlation storage that stores a plurality of two-dimensional correlation tables according to a value of the third signal ratio, the two-dimensional correlation tables indicating a correlation between the first and second signal ratios and the oxygen saturation,
wherein the processor device selects the specific correlation table according to the value of the third signal ratio from the plurality of correlation tables, and calculates the oxygen saturation using the first and second signal ratios and the selected specific correlation table.

3. The endoscope system according to claim 2, wherein the fourth wavelength band includes an isosbestic point at which the amount of light absorption with respect to the oxygen saturation of blood hemoglobin is fixed.

4. The endoscope system according to claim 2, the processor device further configured to
generate a warning signal for giving a warning when the third signal ratio is a value in a specific range set in advance.

5. The endoscope system according to claim 1, further comprising:
a correlation storage that stores a three-dimensional correlation table indicating a correlation between the first to third signal ratios and the oxygen saturation,
wherein the processor device calculates the oxygen saturation according to the first to third signal ratios using the three-dimensional correlation table.

6. The endoscope system according to claim 5, wherein the fourth wavelength band includes an isosbestic point at which the amount of light absorption with respect to the oxygen saturation of blood hemoglobin is fixed.

7. The endoscope system according to claim 5, the processor device further configured to
generate a warning signal for giving a warning when the third signal ratio is a value in a specific range set in advance.

8. The endoscope system according to claim 1, wherein the fourth wavelength band includes an isosbestic point at which the amount of light absorption with respect to the oxygen saturation of blood hemoglobin is fixed.

9. The endoscope system according to claim 1, further comprising:
a warning notification unit that generates a warning signal for giving a warning when the third signal ratio is a value in a specific range set in advance.

10. The endoscope system according to claim 1, the processor device further configured to
generate an oxygen saturation image showing the oxygen saturation; and
generate a display image signal for displaying the oxygen saturation image on a display unit,
wherein the processor device makes a display in a pixel where the third signal ratio is within the specific range and a display in a pixel where the third signal ratio is outside the specific range different from each other based on the warning signal.

11. The endoscope system according to claim 10, wherein the processor device generates the oxygen saturation image in which a color difference signal of the pixel where the third signal ratio is within the specific range is set to zero and a color difference signal of the pixel where the third signal ratio is outside the specific range is set to a value corresponding to the oxygen saturation.

12. The endoscope system according to claim 1, wherein the first and fourth wavelength bands are wavelength bands of 350 nm or more and 500 nm or less.

13. The endoscope system according to claim 1, wherein the first and fourth wavelength bands are wavelength bands of 450 nm or more and 650 nm or less.

14. An endoscope system processor device for an endoscope system, comprising:

a processor device that acquires a first image signal corresponding to a first wavelength band where an amount of light absorption changes according to oxygen saturation of blood hemoglobin, a second image signal corresponding to a second wavelength band where the amount of light absorption changes according to a blood volume of an observation target, a third image signal corresponding to a third wavelength band where a change in the amount of light absorption with respect to the oxygen saturation is small compared with the first image signal and a change in the amount of light absorption with respect to the blood volume is small compared with the second image signal, and a fourth image signal corresponding to a fourth wavelength band, a difference between a center wavelength of the first wavelength band and a center wavelength of the fourth wavelength band being 20 nm or more and 100 nm or less, the processor device calculates oxygen saturation of the observation target for each pixel based on the first image signal, the second image signal, the third image signal, and the fourth image signal, and the processor device calculates, for each pixel, a first signal ratio that is a ratio of the first image signal to the second image signal, a second signal ratio that is a ratio of the third image signal to the second image signal, and a third signal ratio that is a ratio of the second image signal to the fourth image signal, wherein the processor device calculates the oxygen saturation based on the first signal ratio, the second signal ratio, and the third signal ratio.

15. An operation method for an endoscope system, comprising:

a step of acquiring a first image signal corresponding to a first wavelength band where an amount of light absorption changes according to oxygen saturation of blood hemoglobin, a second image signal corresponding to a second wavelength band where the amount of light absorption changes according to a blood volume of an observation target, a third image signal corresponding to a third wavelength band where a change in the amount of light absorption with respect to the oxygen saturation is small compared with the first image signal and a change in the amount of light absorption with respect to the blood volume is small compared with the second image signal, and a fourth image signal corresponding to a fourth wavelength band using a processor device, a difference between a center wavelength of the first wavelength band and a center wavelength of the fourth wavelength band being 20 nm or more and 100 nm or less;

a step of calculating oxygen saturation of the observation target for each pixel based on the first image signal, the second image signal, the third image signal, and the fourth image signal using the processor device; and a step of calculating, for each pixel, a first signal ratio that is a ratio of the first image signal to the second image signal, a second signal ratio that is a ratio of the third image signal to the second image signal, and a third signal ratio that is a ratio of the second image signal to the fourth image signal using the processor device, wherein the processor device calculates the oxygen saturation based on the first signal ratio, the second signal ratio, and the third signal ratio.

16. An operation method for an endoscope system processor device, comprising:

a step of acquiring a first image signal corresponding to a first wavelength band where an amount of light absorption changes according to oxygen saturation of blood hemoglobin, a second image signal corresponding to a second wavelength band where the amount of light absorption changes according to a blood volume of an observation target, a third image signal corresponding to a third wavelength band where a change in the amount of light absorption with respect to the oxygen saturation is small compared with the first image signal and a change in the amount of light absorption with respect to the blood volume is small compared with the second image signal, and a fourth image signal corresponding to a fourth wavelength band using a processor device, a difference between a center wavelength of the first wavelength band and a center wavelength of the fourth wavelength band being 20 nm or more and 100 nm or less;

a step of calculating oxygen saturation of the observation target for each pixel based on the first image signal, the second image signal, the third image signal, and the fourth image signal using the processor device; and a step of calculating, for each pixel, a first signal ratio that is a ratio of the first image signal to the second image signal, a second signal ratio that is a ratio of the third image signal to the second image signal, and a third signal ratio that is a ratio of the second image signal to the fourth image signal using the processor device, wherein the processor device calculates the oxygen saturation based on the first signal ratio, the second signal ratio, and the third signal ratio.

* * * * *